US011883296B2

(12) United States Patent
Morgenstern Lopez et al.

(10) Patent No.: US 11,883,296 B2
(45) Date of Patent: Jan. 30, 2024

(54) PROCESS OF BONE CREATION BETWEEN ADJACENT VERTEBRAE

(71) Applicant: Endospine, S.L., Parroquia de Canillo (AD)

(72) Inventors: Rudolf Morgenstern Lopez, Esplugues de Llobregat (ES); Christian Rudolf Morgenstern De Muller, Esplugues de Llobregat (ES)

(73) Assignee: Endospine, S.L., Parroquia de Canillo (AD)

( * ) Notice: Subject to any disclaimer, the term of this patent is extended or adjusted under 35 U.S.C. 154(b) by 120 days.

(21) Appl. No.: 17/656,326

(22) Filed: Mar. 24, 2022

(65) Prior Publication Data

US 2022/0211504 A1    Jul. 7, 2022

Related U.S. Application Data

(63) Continuation of application No. 16/331,793, filed as application No. PCT/ES2017/070712 on Oct. 24, 2017, now abandoned.

(30) Foreign Application Priority Data

Nov. 7, 2016  (ES) ................. ES201631413

(51) Int. Cl.
*A61B 17/70* (2006.01)
*A61B 17/86* (2006.01)
(Continued)

(52) U.S. Cl.
CPC ............... *A61F 2/28* (2013.01); *A61F 2/446* (2013.01); *A61L 24/0015* (2013.01);
(Continued)

(58) Field of Classification Search
None
See application file for complete search history.

(56) References Cited

U.S. PATENT DOCUMENTS

| 4,456,005 A | 6/1984 | Lichty |
| 5,217,462 A | 6/1993 | Asnis et al. |

(Continued)

FOREIGN PATENT DOCUMENTS

| CA | 2515862 A1 | 9/2004 |
| CN | 101239182 A | 8/2008 |

(Continued)

OTHER PUBLICATIONS

Chinese Office Action issued in the corresponding Chinese Patent Application No. 201780057558.5, dated Jan. 5, 2023 in 13 pages.
(Continued)

*Primary Examiner* — Jan Christopher L Merene
(74) *Attorney, Agent, or Firm* — Knobbe, Martens, Olson & Bear, LLP

(57) ABSTRACT

A process of bone creation between adjacent vertebrae uses an intervertebral stabilizing screw, which includes a main body with an axial through hole, a distal thread and at least one fill hole. A hollow proximal secondary body of the screw includes an external thread a travel stop. The process includes inserting the main body until the distal thread is secured to an upper vertebrae of the adjacent vertebrae such that the at least one fill hole is in inside of the disk, inserting the proximal body until reaching to the limit stop such that the proximal body is threaded inside of a pedicle and secured to a lower vertebrae of the adjacent vertebrae, and injecting a bone remodeling composition into inside of the disk through the axial hole and the at least one fill hole.

6 Claims, 27 Drawing Sheets

(51) Int. Cl.
  *A61F 2/28* (2006.01)
  *A61F 2/44* (2006.01)
  *A61L 24/00* (2006.01)
  *A61F 2/30* (2006.01)

(52) U.S. Cl.
  CPC ... *A61L 24/0084* (2013.01); *A61F 2002/2835* (2013.01); *A61F 2002/3085* (2013.01); *A61F 2002/30235* (2013.01); *A61F 2002/30593* (2013.01); *A61F 2002/30622* (2013.01); *A61L 2300/412* (2013.01); *A61L 2430/02* (2013.01)

(56) References Cited

U.S. PATENT DOCUMENTS

| | | |
|---|---|---|
| 6,471,707 B1 | 10/2002 | Miller et al. |
| 7,862,593 B2 | 1/2011 | Clement et al. |
| 9,089,371 B1 | 7/2015 | Faulhaber |
| 10,582,952 B2 | 3/2020 | Faulhaber |
| 10,799,367 B2 | 10/2020 | Vrionis et al. |
| 2001/0021852 A1 | 9/2001 | Chappius |
| 2003/0088251 A1 | 5/2003 | Braun et al. |
| 2004/0122431 A1 | 6/2004 | Biedermann et al. |
| 2005/0059972 A1 | 3/2005 | Biscup |
| 2005/0154390 A1 | 7/2005 | Biedermann et al. |
| 2005/0261695 A1 | 11/2005 | Cragg et al. |
| 2007/0161985 A1 | 7/2007 | Demakas et al. |
| 2007/0276402 A1 | 11/2007 | Laboratories et al. |
| 2010/0004690 A1 | 1/2010 | Cragg et al. |
| 2010/0036440 A1 | 2/2010 | Morris et al. |
| 2010/0036495 A1* | 2/2010 | Daum .................. A61F 2/4611 623/17.11 |
| 2010/0268285 A1 | 10/2010 | Tipirneni et al. |
| 2010/0298889 A1 | 11/2010 | Wilberg et al. |
| 2011/0040329 A1 | 2/2011 | Ainsworth et al. |
| 2011/0118785 A1* | 5/2011 | Reiley ................ A61B 17/1615 606/279 |
| 2011/0118790 A1 | 5/2011 | Reiley |
| 2011/0282387 A1 | 11/2011 | Suh et al. |
| 2013/0131733 A1 | 5/2013 | Chien et al. |
| 2013/0345763 A1 | 12/2013 | Kang |
| 2014/0031934 A1 | 1/2014 | Trieu |
| 2014/0178328 A1 | 6/2014 | D'Agostino et al. |
| 2014/0194886 A1 | 7/2014 | Nicholas |
| 2016/0081721 A1 | 3/2016 | Faulhaber |
| 2016/0220291 A1 | 8/2016 | Russell et al. |
| 2016/0287301 A1 | 10/2016 | Mehl et al. |
| 2016/0310188 A1 | 10/2016 | Marino et al. |
| 2016/0310190 A1* | 10/2016 | Gonzalez Blohm ... A61B 17/70 |
| 2017/0119446 A1* | 5/2017 | Suh ....................... A61B 17/864 |
| 2018/0092751 A1* | 4/2018 | Vrionis .............. A61B 17/8685 |
| 2018/0317989 A1 | 11/2018 | Sellers |

FOREIGN PATENT DOCUMENTS

| | | |
|---|---|---|
| DE | 102018101843 A1 * | 8/2019 |
| FR | 3 013 581 A1 | 5/2015 |
| WO | WO 2005/041793 A2 | 5/2005 |

OTHER PUBLICATIONS

Joukar et al., "Biomechanics of the Sacroiliac Joint: Surgical Treatments"; International Journal of Spine Surgery, vol. 14, No. 3, pp. 355-367, (2020).

International Search Report for PCT Application No. PCT/ES2017/070712, dated Feb. 23, 2018 in 12 pages.

European Search Report for European Application No. EP 17 86 6442, dated Mar. 27, 2020 in 10 pages.

* cited by examiner

PROCESS OF BONE CREATION BETWEEN ADJACENT VERTEBRAE

CROSS-REFERENCE TO RELATED APPLICATIONS

This application is a continuation of U.S. application Ser. No. 16/331,793, filed on Mar. 8, 2019 as the U.S. National Phase under 35. U.S.C. § 371 of International Application PCT/ES2017/070712, filed Oct. 24, 2017, which claims priority to Spanish Patent Application No. 201631413, filed Nov. 7, 2016. The disclosures of the above-described applications are hereby incorporated by reference in their entirety.

FIELD OF THE INVENTION

The present invention relates to an intervertebral fusion device comprising an intervertebral stabilising screw and a composition for bone remodelling, to said screw and to said composition.

BACKGROUND OF THE INVENTION

The process of bone creation between adjacent vertebrae, thus connecting said vertebrae together, is known as vertebral fusion or arthrodesis.

Intervertebral fusions are performed at present by putting in place a bone graft either from the patient him or herself (normally from the vertebra concerned or from the iliac crest) or from another (external or artificial) source. The graft may be secured to the affected vertebrae by screws. In addition, a structure for securing to the affected vertebrae must be put in place which comprises bars or plates that follow the shape of the spinal column and are secured to each vertebra by screws (subsequent instrumentation). Said structure is needed to overcome the intervertebral instability (spondylolisthesis) usually associated with these conditions and to protect the graft during the consolidation (bone creation) phase. This operation normally requires open surgery. Intervertebral fusion or bone consolidation continues for months or years, and in some cases does not produce anything (pseudoarthrosis). 100% effective healing is not necessarily the norm. The structure for securing to the affected vertebrae, despite being somewhat conspicuous, is only removed in cases where said structure causes considerable inconvenience and only once completely satisfactory bone mineral consolidation that can be verified by radiological techniques has taken place.

SUMMARY OF THE INVENTION

An object of the present invention is to disclose a device for immediate intervertebral fusion (vertebral fusion device) which provides a solution to the problems raised. In particular, the vertebral fusion device allows fusions to be carried out immediately using percutaneous techniques and outpatient surgical centres. The novel fusion device eliminates the need for subsequent instrumentation to protect the area from movements during the bone consolidation phase and provides a solution to the problems that occur when on occasion bone formation fails. Local anaesthesia may be used. The novel fusion device also eliminates the need for other metal inserts which project from the spinal column and may be the source of problems. The novel fusion device also allows some correction of intervertebral displacements. The novel fusion device comprises, in combination, a novel intervertebral stabilising screw and a novel composition for bone remodelling which comprises a bone cement. Both the screw and the bone remodelling composition are novel and can usually be developed and manufactured by different technical teams.

The present invention is particularly applicable to spondylolisthesis at any level, whether single or multiple, although it can also be applied to the treatment of other spinal pathologies. In a general case, the device according to the present invention may be installed using percutaneous techniques and even without the need to dilate soft tissue to facilitate surgical access.

To do this, the present invention also discloses a bone remodelling composition which produces a bed which promotes bone formation in difficult growth conditions inside the intervertebral ring (disk) and an insert (formed typically by two screws for each fused level) which allows said bed to be positioned in the intervertebral disk space and which cooperates with the bed in stabilising the intervertebral area during the bone formation phase. During the bone formation phase, stabilisation and preservation of the intervertebral space take place in conjunction, both through the insert or inserts and through the bone cement contained in the bone remodelling composition.

The bone remodelling composition according to the present invention is based on the use of what is known as bone cement. Different types of bone cements are known, generally biocompatible polymers which are polymerised during application. Polymerisation 'in situ' allows application in a liquid state and the subsequent, immediate hardening thereof. Although the word 'cement' is used in the sector, it should be noted that this does not imply connection of the cement to the bone, but rather the cement simply fills the existing hollow. In other words, bone cements could also be referred to generally as 'mortar' or 'filler' rather than 'cement'.

Bone cements are used in orthopaedic surgery as an implant or for remodelling lost bone. Said bone cements are also used to fill vertebral fractures. When the cement hardens, the continuous pain associated with the fracture is alleviated.

Among known cements are poly(methyl methacrylate) (PMMA), bisphenol A-glycidyl methacrylate (bis-GMA) and poly(lactic-co-glycolic acid) (PLGA). The use of PMMA is the most widespread. By suitable selection of initiators and monomers, commercial versions are marketed with a polymerisation temperature that is very close to body temperature, which is advisable to prevent thermal necrosis of the surrounding tissue. Equipment is also supplied to control the viscosity of the cement during the initial phases of polymerisation, so as to control the injection thereof. An example of a commercial polymerisable bone cement that allows said control is the one marketed under the name StabiliT®.

In '*Targeted therapy of low back pain associated with de novo degenerative lumbar scoliosis in the elderly: prospective observation cohort study*' (Eur Spine J (2014) 23 (Suppl 5):S496-S496), Yamada et al. disclosed the percutaneous transpedicular injection of PMMA. Yamada applies the cement using an 11 G needle to very painful degenerated disks but where the integrity of the ring is preserved and $N_2$ is formed inside said ring, which is not usually the case. Yamada does not carry out cleaning of the nucleus and restricts himself to filling existing hollows. This technique does not involve vertebral fusion with bone formation, but rather putting cement in place as an insert, which prevents the vertebrae from coming closer together. As already mentioned, if connection of the insert in the space occurs, this may be problematic. In addition, the technique is only applicable if the intervertebral space has not be damaged or significantly reduced.

A problem associated with bone cements, in particular with PMMA, and therefore with the Yamada technique, is that its Young modulus is very different to that of human bone, and therefore stresses are concentrated in the cement. As the nearby bone lacks stress stimulation, resorption of said bone might occur, which in turn may cause new fractures in the bone surrounding the bone cement. Ultimately, the lifespan of the bone cement prosthesis may be limited.

The addition of hydroxyapatite to bone cement is known in order to make the physical properties of the bone cement more like those of bone. For example, in '*PMMA-hydroxyapatite composite material increases lifetime of augmented bone and facilitates bone apposition to PMMA: Biomechanical and histological investigation using a sheep model*' (European Cells and Materials Vol. 28 Suppl. 1, 2014 (page 15), Arbmotlagh et al. found that the addition of 30% hydroxyapatite improved the cycles until the failure of the surrounding bone compared with the use of PMMA alone. The histological section at six months found weak areas of bone within the PMMA matrix when hydroxyapatite was used with PMMA.

Furthermore, vertebral stabilising screws are also known, for example that known commercially as Perpos®. This screw is intended for installation by passing through the facet of a vertebra and being inserted in the pedicle of the lower vertebra (without affecting the vertebral ring). The vertebral stabilising screw comprises a distal thread intended to be threaded into the vertebra, in the area of the pedicle. Said screw also comprises an axial through-hole which is used for guiding the screw. The screw also comprises a proximal portion which is able to move on the main body, the function of which is to adjust the operating length of the screw. The screw comprises a locking mechanism or catch which secures the proximal portion at the required point of travel along the length of the main body.

According to another aspect, the present invention also discloses an intervertebral stabilising screw which comprises a main body with an axial through-hole (cannulated screw) and a distal thread for securing to the bone, located at a distal end of the main body, a hollow proximal secondary body that can slide along the length of the main body and a travel stop for the proximal secondary body, located on an outer surface of the main body, in which the proximal secondary body also includes an external thread for securing to the bone, and between the distal thread and said main body comprises at least one fill hole, located between the distal thread and said stop, for connecting an intervertebral space to said axial hole.

The screw according to the present invention comprises two threads, each intended to be threaded to contiguous vertebrae. The area between the distal thread and the limit stop is intended to remain within the space of the intervertebral ring. The fill hole allows the intervertebral space (intra-annular space) to be filled with a bone remodelling composition. The thread of the proximal secondary body (proximal thread) allows the screw to be secured to a vertebra that is adjacent to the vertebra that receives the distal thread.

According to the present invention, the preferred installation of the screw may be carried out in a transpedicular manner. The present invention provides for the insertion of two screws, one on either side, for each level to be fused. In this arrangement, the screws, owing to the proximal thread, allow lordosis and lateral deviations of the spine to be corrected before the injection of the bone remodelling composition.

The present invention provides, preferably, for the outer diameter of the thread of the proximal secondary body (proximal thread) to have a greater diameter than the diameter of the distal thread. Thus the distal thread passes more easily through the proximal thread installation area, without impairing the securing of the proximal thread to the bone of the vertebra and also moving the main body of the screw, by pushing said screw to thread the secondary body into the lower vertebra.

The limit stop may take different forms and the function thereof is to prevent the proximal secondary body from blocking the fill hole or holes during its travel. Preferably, the main body has a step which performs said function. Said step may be obtained, preferably, by a variation in the external diameter of the main body. The proximal body can therefore slide around the area with the smaller external diameter, but not through the area with the greater external diameter.

The course of the fill holes is preferably radial, which minimises the length thereof. To provide the fill function, the main body has at least two fill holes. Very preferably, the course of the fill holes is diametric, with two outlets which connect opposite points of the wall of the main body. This arrangement allows the doctor who is carrying out the operation to check that there is at least one hole in the intervertebral space. To do this, the doctor must orient the screw so that the diametric direction of the hole coincides with the emission direction of the X-rays from the fluoroscope. The hole will therefore be visible using the fluoroscope.

The present invention also provides for the screw to also have a cover to close off access to the axial hole once the bone cement has been injected.

To facilitate the placement thereof by percutaneous surgery, the present invention provides for both the main body and the proximal body to have a device at the proximal end thereof for receiving a percutaneous tool, such as a hexagonal or similar screwdriver.

In particularly preferred embodiments, the main body and the proximal secondary body are threaded together. In this way, said sliding along the length of the main body is associated with a relative rotation between the main body and the proximal secondary body. This allows the bodies to be actuated by means of concentric, percutaneous sleeves, facilitating the forward and backward motion of both bodies simultaneously in both of the vertebrae in which said bodies are situated. The thread mechanism between the two bodies makes possible the additional distraction or contraction of the intervertebral space as required by the surgeon. This arrangement also allows the selective injection of the cement from the most distal point to the most proximal portion by moving the cement or composition injector forwards or backwards through both bodies at the same time.

The bone remodelling composition according to the present invention comprises polymerisable bone cement, a calcium phosphate provider and an oxygen-providing compound. Preferably said composition also comprises an osteogenic factor and/or a contrast agent.

The oxygen-providing compound in the composition according to the present invention has the dual function of increasing the porosity of the bone cement, creating hollows in the polymeric matrix of the cement and of providing the oxygen required to stimulate bone formation. This allows not only the formation of bone in an area such as the intervertebral area without supplying blood, but also leaves space for the coherent formation of said bone. The oxygen-providing compound may preferably be oxygenated water, ozone or an oxygen solution. More preferably, said oxygen-providing compound is oxygenated water. Oxygenated water has the advantage of being liquid, and of breaking down into water and oxygen under suitable conditions, which allows said oxygenated water to be mixed with the bone cement and injected during the bone cement polymerisation process.

The hollows produced by the release of oxygen help ensure that the bed formed by the bone cement matrix has mechanical properties that are very similar to those of bone.

The polymerisable bone cement may be of any type, but those that comprise at least one of the following: poly(methyl methacrylate) (PMMA), bisphenol A-glycidyl methacrylate (bis-GMA) and poly(lactic-co-glycolic acid) (PLGA) are preferable. More preferably, the polymerisable bone cement comprises PMMA. PLGA may also be preferred owing to its biocompatibility.

The calcium phosphate-providing substance may preferably be hydroxyapatite, brushite, calcium phosphate or tricalcium phosphate. Hydroxyapatite is preferable owing to its superior biocompatibility and because it is the main form in which calcium phosphate is found in bone. The preferred functions of the calcium phosphate provider are to promote bone formation and to render the properties of the bed of bone cement more like those of bone, in order to minimise the possibility of fracture of the bone surrounding the vertebral platforms.

The osteogenic factors promote and establish the bone creation pathways. Preferably, the osteogenic factor in the composition according to the present invention comprises at least one of the following: whole blood, blood-derived growth factors and osteogenic stem cells. Blood-derived growth factors are preferred owing to the efficacy and ease of obtaining said blood-derived growth factors.

The components of the composition according to the present invention may be present in any proportion.

Preferably, the calcium phosphate provider is between 30% and 15% by weight.

Preferably, the oxygenated water is present in a quantity equal to or less than 5% by weight. Also preferably, the osteogenic factor is present in a quantity of less than 5% by weight. Also preferably, the contrast is present in a quantity of less than 5% by weight, more preferably in a quantity of less than 1% by weight.

The polymerisable bone cement will preferably be present in a quantity of between 55% and 80% depending on the rest of the components present and on the hardness required for the bed that is to be formed.

Particularly preferably, the presence of a contrast agent, preferably a non-ionic contrast agent, allows the placement of the composition in the disk space to be controlled during an operation to install the device according to the present invention percutaneously.

Thus, the vertebral fusion device comprises the bone remodelling composition according to the present invention and at least one screw, preferably at least two screws.

The device according to the present invention may be installed using percutaneous techniques, preferably by guiding the vertebral stabilising screws. Installation comprises, preferably, the phases of cleaning the disk space, scraping, and the transpedicular installation of the screws; if necessary, correction of the relative position of the vertebrae by threading the proximal thread against the limit stop and injecting the bone remodelling composition into the intervertebral space through the axial hole and the fill hole. To facilitate bone formation from the vertebrae, the vertebral platforms must be scraped with a flexible or bendable osteotome, before introducing the bone remodelling composition.

The use of one or two screws for transpedicular access helps preserve the integrity of the intervertebral disk and, in particular, the seal of the disk ring during surgical access of the intradiskal space, thus allowing the bone remodelling composition to be injected without causing leaks thereof before final solidification. The preservation of the seal and the immediate solidification (polymerisation) make it possible to achieve an immediate fusion which until now was impossible using conventional intervertebral arthrodesis surgical techniques.

BRIEF DESCRIPTION OF THE DRAWINGS

For a better understanding, the accompanying drawings of two embodiments of the subject of the present invention are provided by way of non-limiting example.

DETAILED DESCRIPTION OF THE PREFERRED EMBODIMENTS

Figure 1:
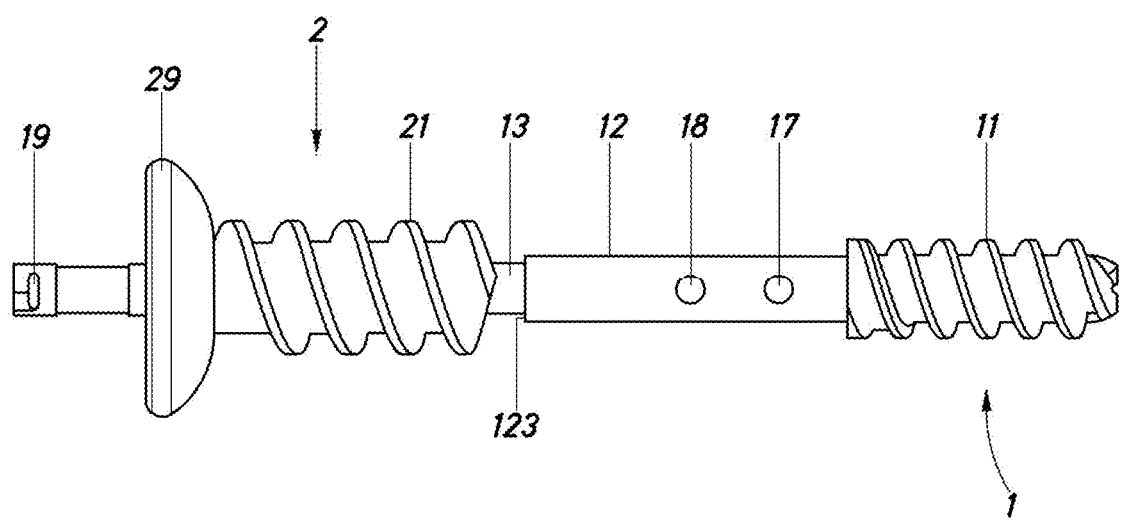
FIG. 1 is a side view of an embodiment of a screw according to the present invention.
Figure 2:
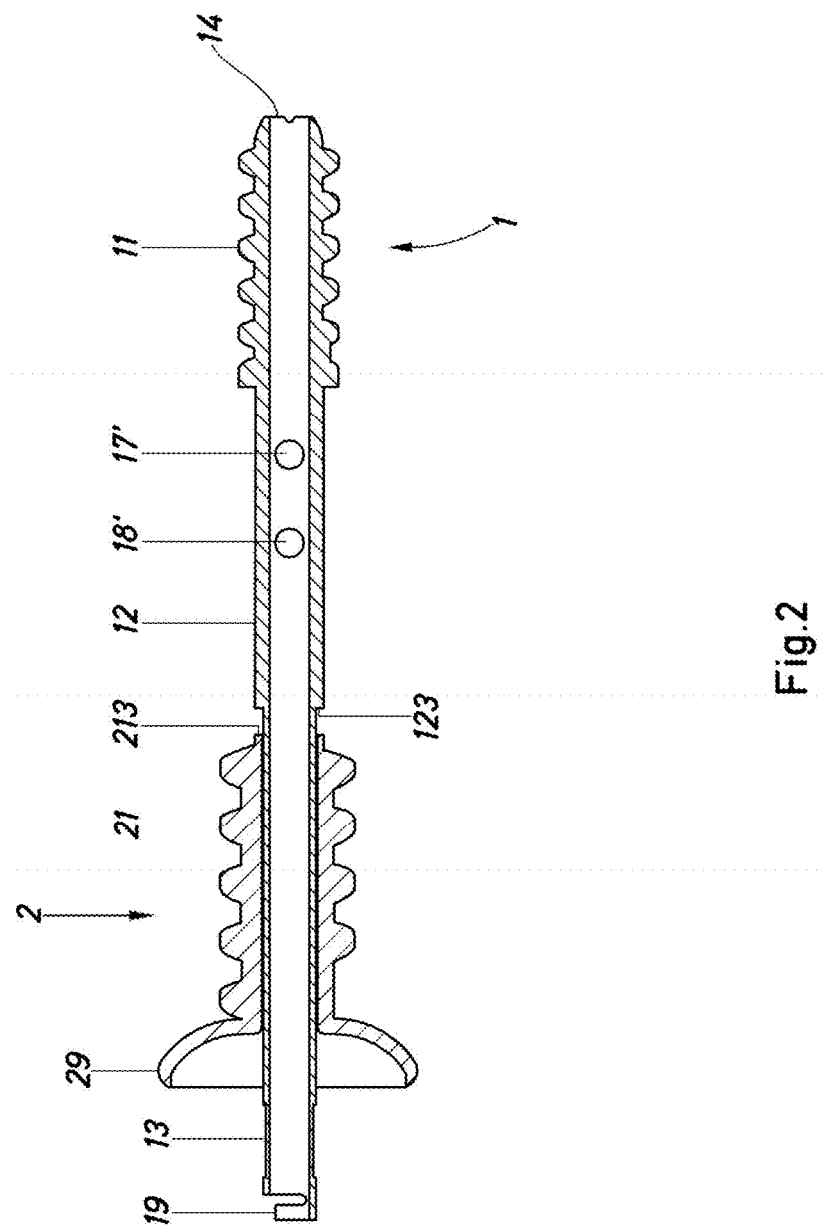
FIG. 2 is a view in cross section through the lateral mid-plane of the screw of FIG. 1.
Figure 3:
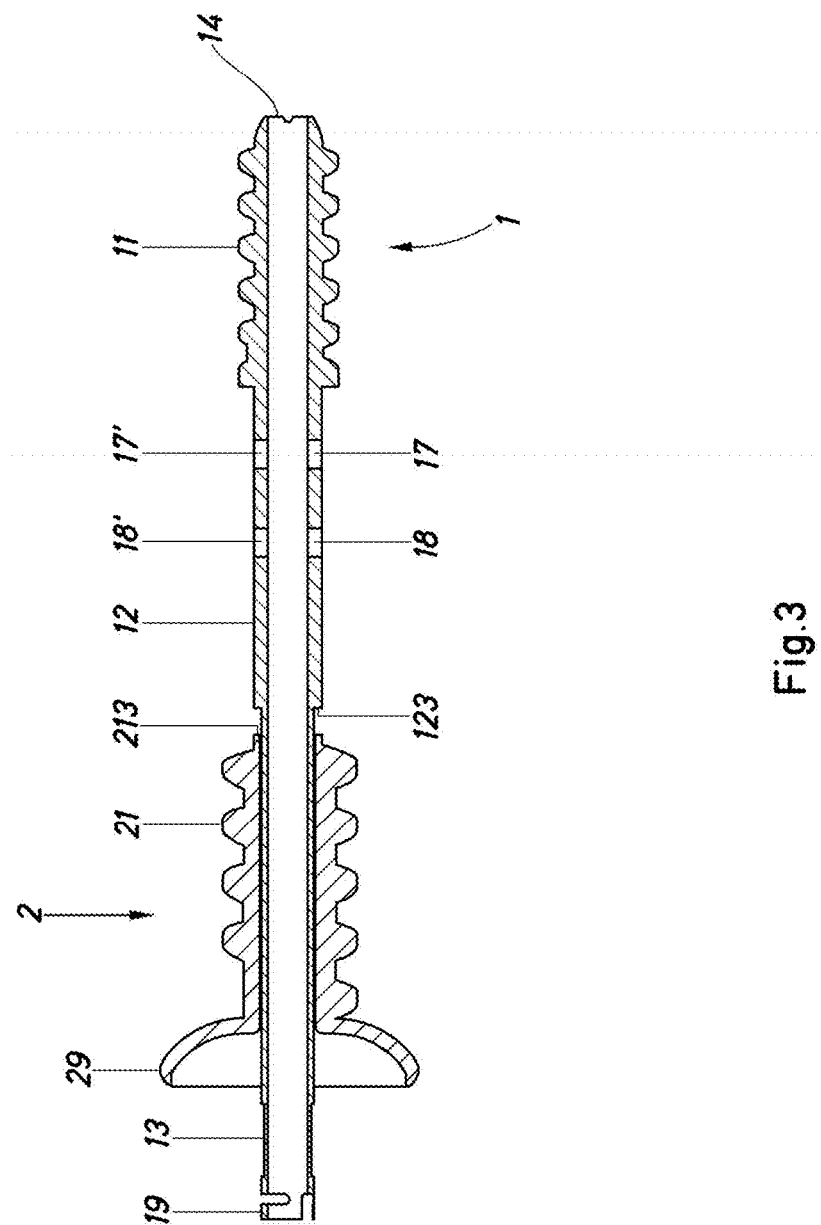
FIG. 3 is a view in cross section through a mid-plane perpendicular to the cutting plane of FIG. 2.

FIG. 1 to 3 show an embodiment of a screw according to the present invention.

The example of a screw shown in the figures comprises two parts that can move relative to one another: a main body -1- and a proximal secondary body, hereinbelow, a proximal body -2-. The proximal body -2- slides along the length of the main body, in an axial direction. The references to distal and proximal take as their reference the transcutaneous process of placing a screw in a patient.

The main body -1- has at its distal end a distal thread -11- for securing to bone. The rest of the main body is separated into two areas -12-, -13- separated by a limit stop -123- formed by a step produced by a sudden change in the external diameter thereof. A proximal body -2-, which also has a proximal thread -21- for securing to bone, is able to travel over the outside of the most proximal area -13-. Since the proximal thread -21 must be secured to bone in an area through which the distal thread -11- has already passed, it may be advantageous for the external diameter of the proximal thread -21- to be greater than that of the distal thread -11-, in order to improve securing. The limit of travel of the proximal portion -2- is defined by the interference of the most distal face -213- thereof with the limit stop -123-.

Both the main body -1- and the proximal body -2- have at their proximal ends areas or devices -19-, -29- which allow said bodies to be suitably operated using percutaneous devices. It will be appreciated that said areas may be different from those shown.

Both the main body -1- and the proximal body -2- are hollow, and have an axial hole. In the case of the proximal body, this allows said body to slide along the length of the main body -1-, but it would also be possible, alternatively, for both bodies to be threaded together.

The axial hole of the main body terminates in a distal hole -14-. This allows the main body to be guided in its travel. In addition, the example has fill holes arranged diametrically with opposite outlets -17-, 17'-, -18-, -18'- in the area -12- between the limit stop -123- and the distal thread -11-. Said holes will allow the intervertebral space (inside the vertebral disk) to be filled with a bone remodelling composition through the axial hole and the fill holes.

The fill holes preferably have two or more cores and the arrangement thereof may be symmetrical. The ideal fill hole core and the composition thereof depend on the anatomy and vertebral condition of the patient.

Figure 4:
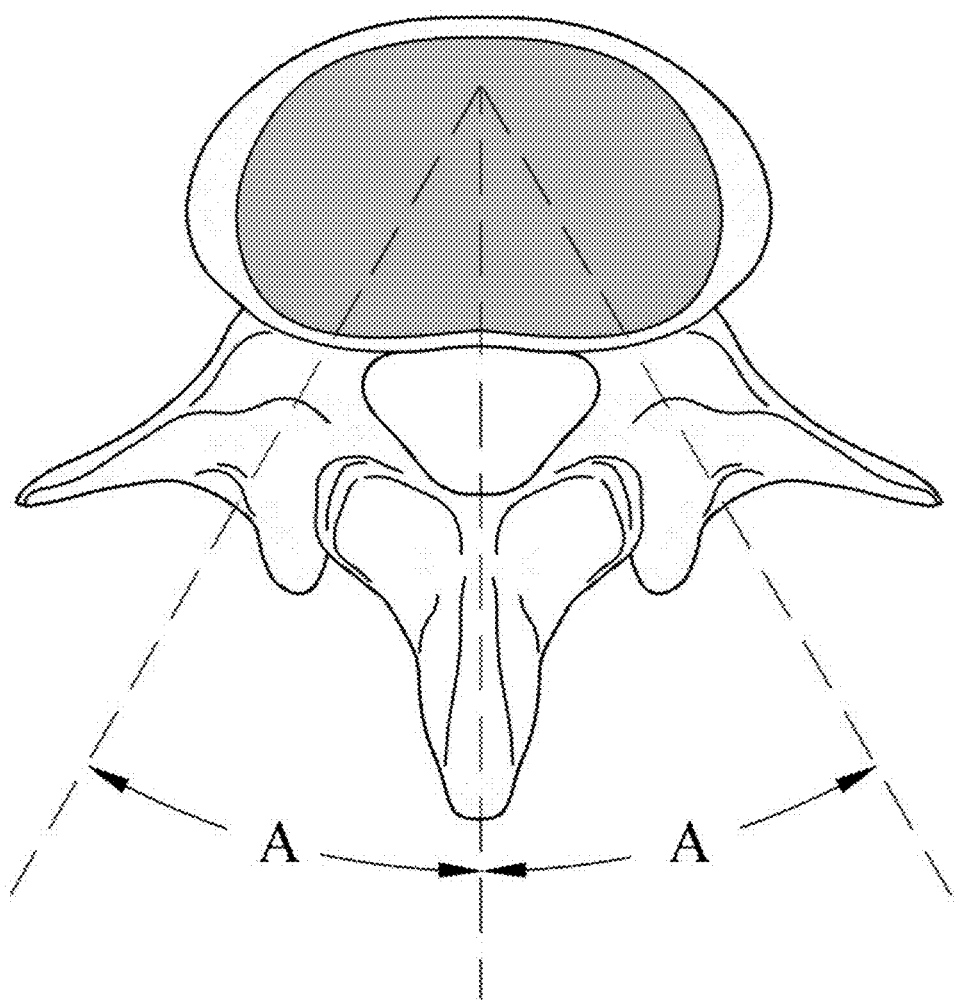
FIG. 4 is a view from a sagittal plane of the vertebral level that will be fused. The figure shows the lower vertebra and the disk space, the upper vertebra having been omitted. The trajectory of introduction of the screw according to the present invention has also been shown.
Figure 5:
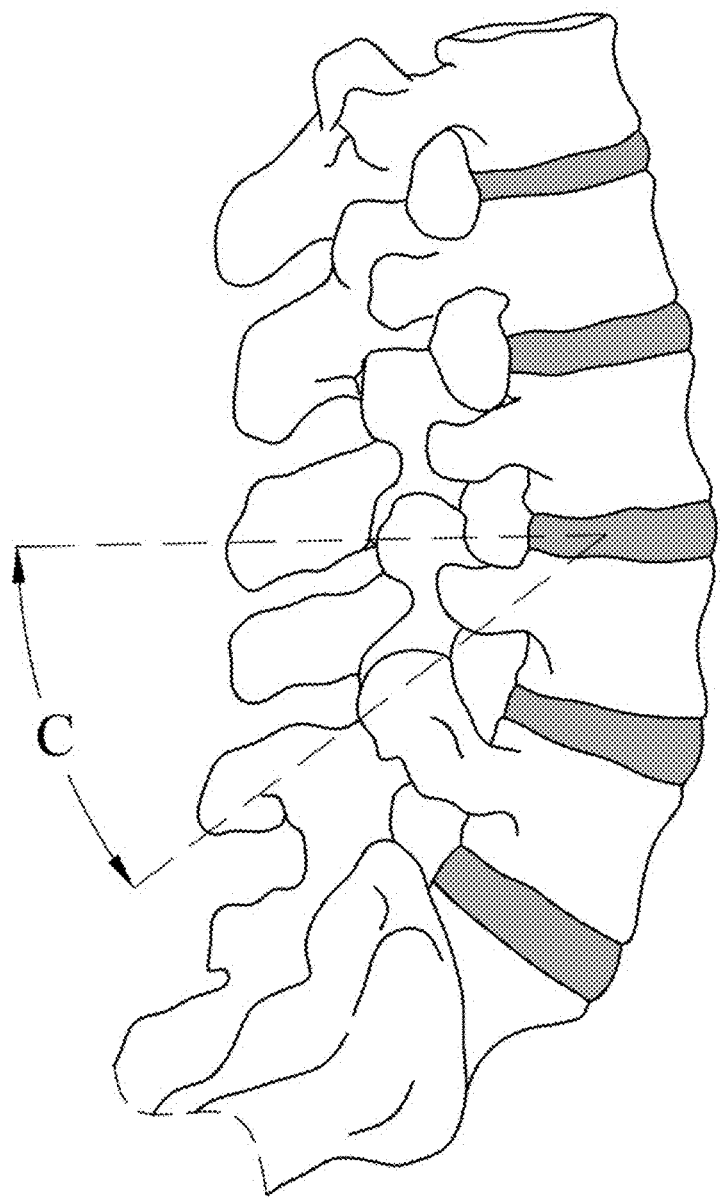
FIG. 5 is a view from an axial plane of the level to be fused of the previous figure, in which the placement trajectory of the screw has also been marked.
Figure 6:
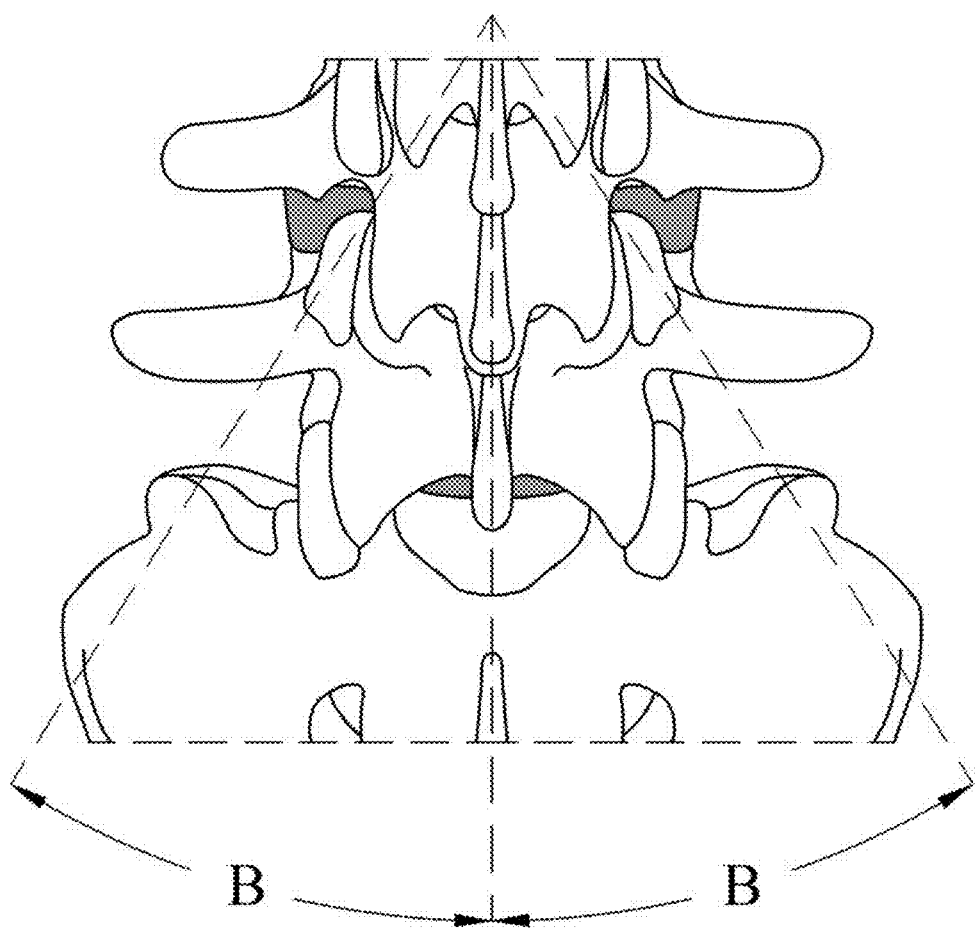
FIG. 6 is a view from a coronal plane of the spine shown in the previous figures, with the placement trajectory of two screws according to the present invention also marked.

FIG. 4 to 6 show the preferred placement trajectory of two screws according to the present invention for fusing a vertebral level. Two screws are sufficient. The introduction thereof is transpedicular, passing through the disk space in such a way that the distal thread will be threaded in the upper vertebra and the proximal thread in the lower vertebra.

The preferred access point for percutaneous placement is situated in the pedicle, in the centre of the upper articular process and approximately 1 mm below the lower edge of the transverse process of the vertebra, varying according to the specific anatomy and other factors.

The angle of introduction (defined by the value of the angles -A-, -B-, -C-) also varies depending on the specific anatomy of the vertebra. An optimal value for an L4-L5 fusion would be 35±5° for each of the three values (-A-, -B-, -C-), more preferably 35°.

FIG. 7 to 14 show an example of an installation process of an embodiment of an intervertebral fusion device according to the present invention.

In said figures, elements that are the same or equivalent to those shown in the previous figures have been identified with identical numerals and will therefore not be explained in detail.

Initially, the guides may be installed following the direction shown in FIG. 4 to 6. For reasons of clarity, the guides have not been shown in any of the figures. For the application shown, an 11G Jamshidi-type trocar may be used for example for accessing and penetrating the pedicle and a Kissner needle as a guide for the placement of the screw. Placement is transcutaneous, bilateral and pedicular. Using fluoroscopic techniques, its passage through the disk space and penetration 5-10 mm into the body of the upper vertebra and through the lower platform of the upper vertebra can be controlled.

At any time in the process (not shown in the figures) it may be useful to check the state of the seal of the ring using radiological discography, in order to verify that the technique is viable and/or to adjust the viscosity of the bone cement.

Figure 7:
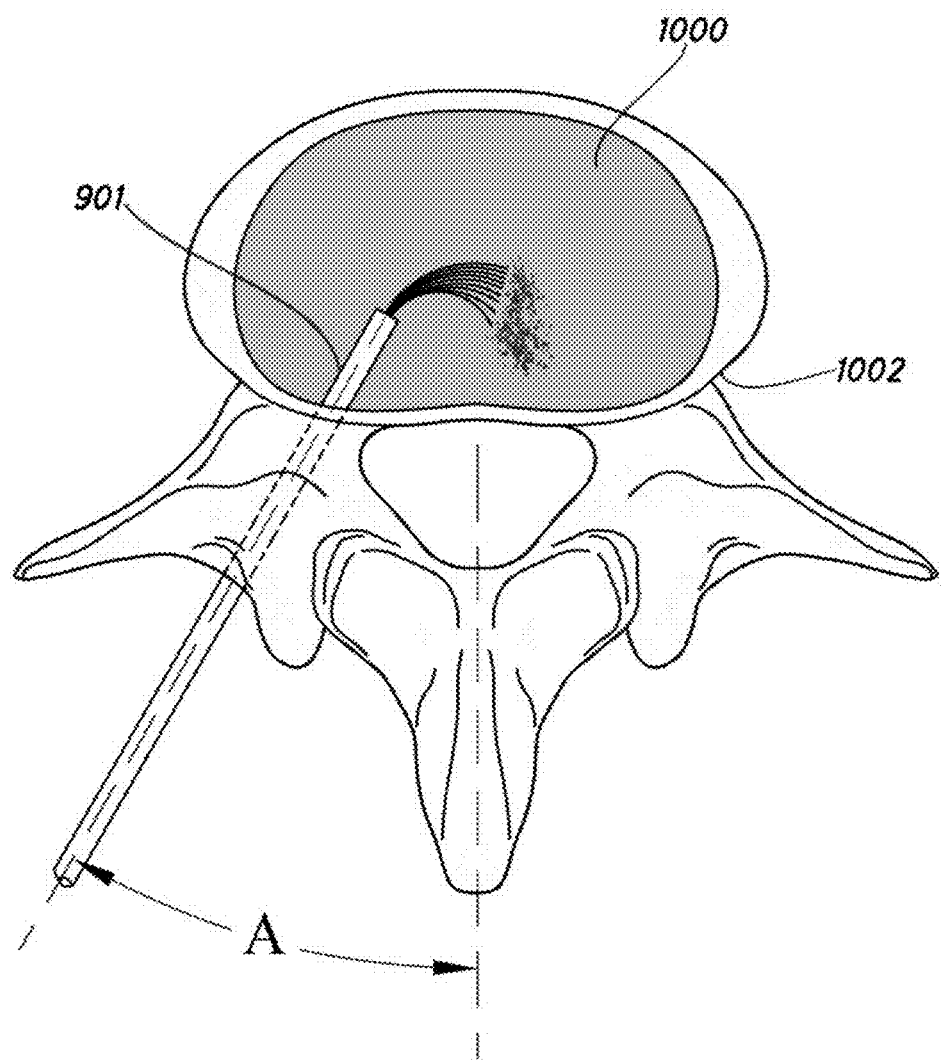
FIG. 7 shows a first phase of an example of the process of putting in place the device according to the present invention, in which the disk content (nucleus) has been omitted.

The process begins with ablation or nucleolisis, for example by radiofrequency, of the material inside the disk -1000-. This can be carried out with a Jamshidi-type cannula, as shown in FIG. 7. This technique appears viable, as it has already been applied to the ablation of metastatic posterior vertebral body osseous tumours using a bipolar device for ablation by radiofrequency. Alternatively, the material may also be removed mechanically. The cannula -901- may have been inserted by guiding, using sufficiently known percutaneous techniques. In the figure, a single cannula has been shown, but two may be inserted, one on either side. This technique has the advantage of making possible the preservation of the disk ring.

Figure 8:
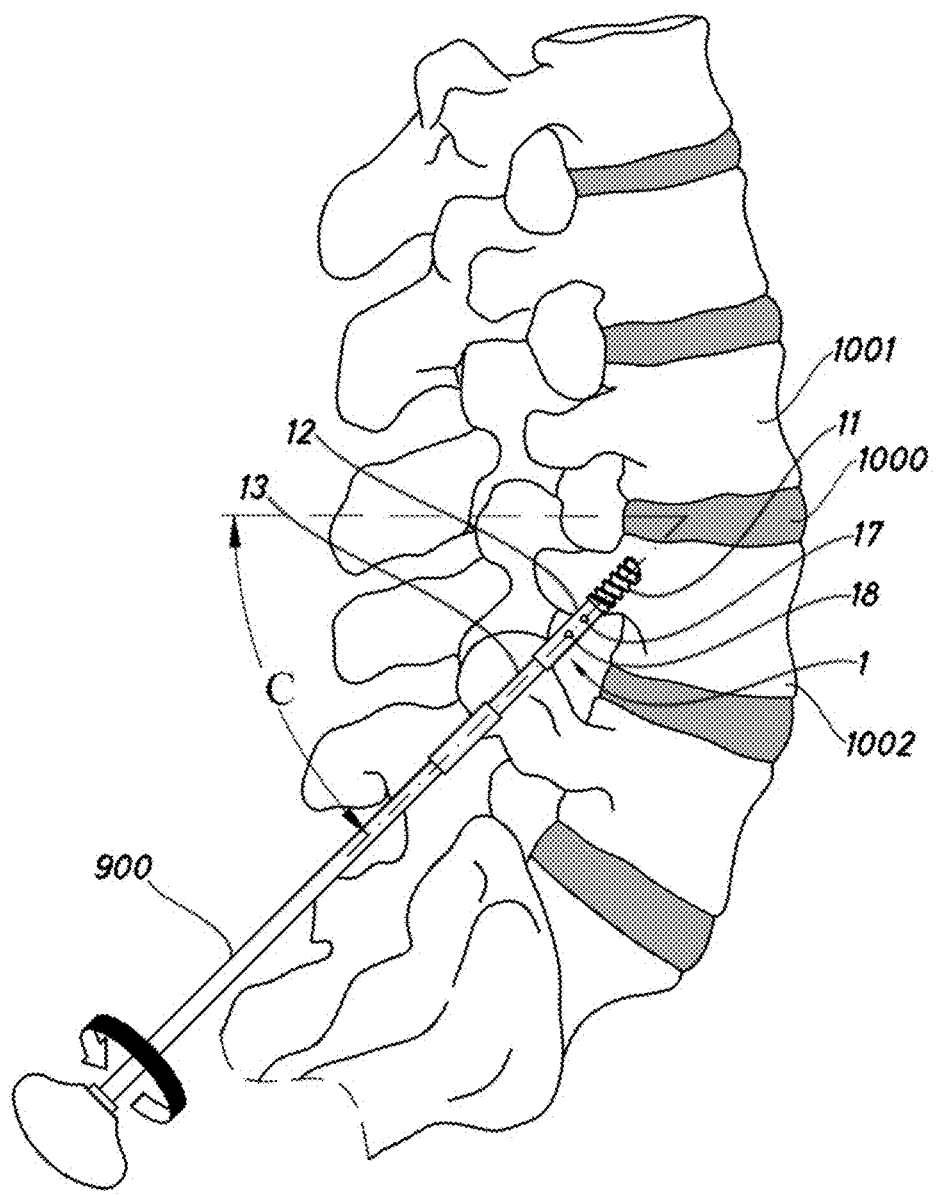
FIG. 8 shows diagrammatically a second phase of the device placement process.
Figure 9:
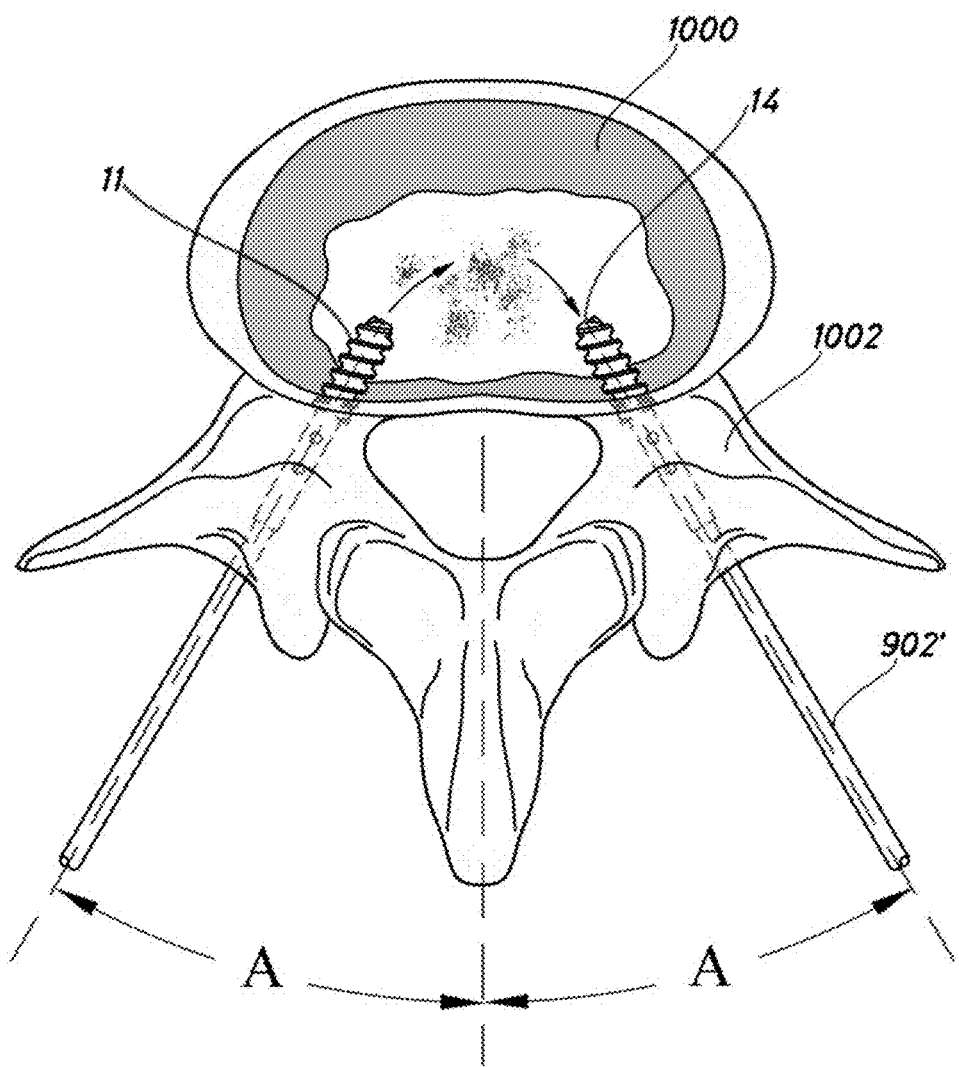
FIG. 9 shows diagrammatically a third phase of the device placement process.

Next the waste disk material produced by the nucleolisis is drawn off. To do this, a cleaning fluid is introduced at one side and removed at the other side, which draws out the waste material. To do this, two transpedicular cannulas may be used such as the cannula -901- shown in FIG. 7, one on either side. In FIGS. 8 and 9 an alternative technique has been shown in which two screws are introduced, said screws being threaded using the appropriate tool -900-, until the distal hole -14- of both screws is situated in the distal space and the cleaning fluid is then circulated through the two axial holes of both screws.

Figure 10:
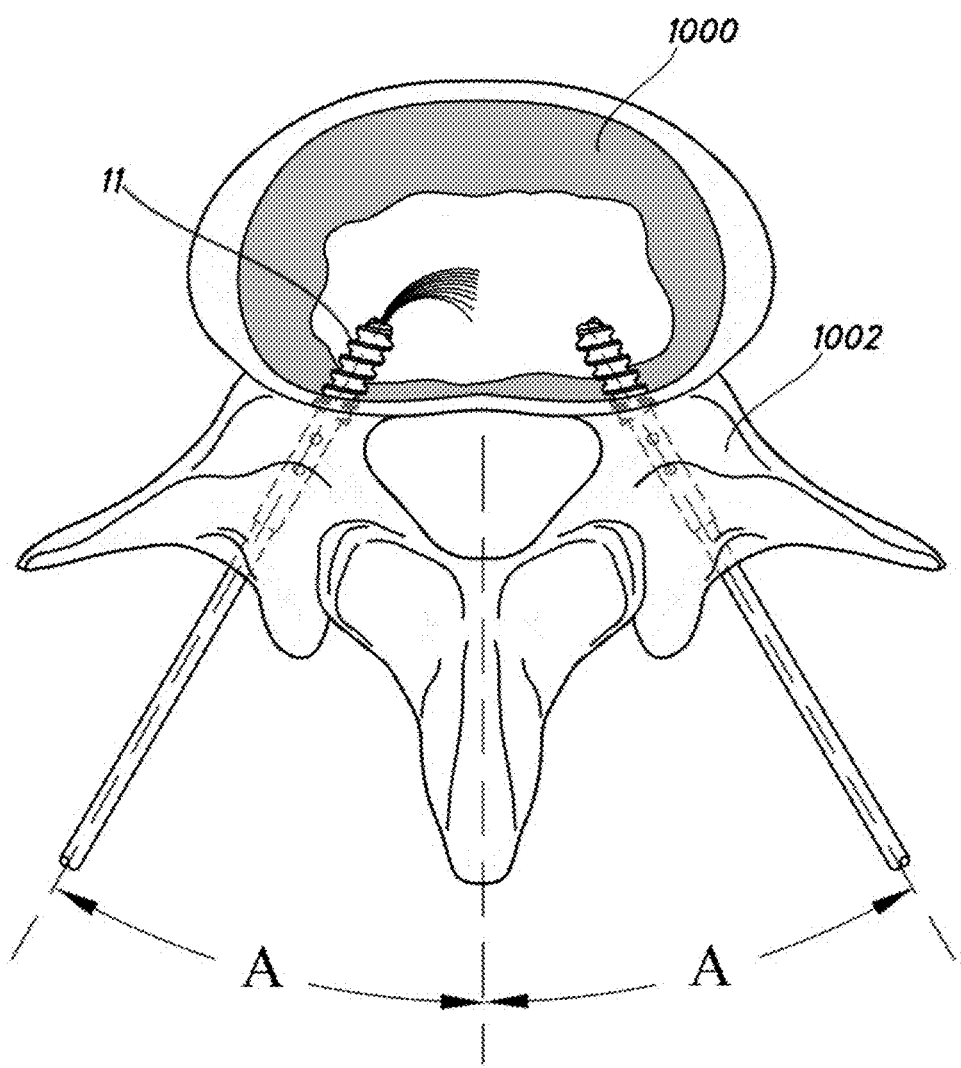
FIG. 10 shows diagrammatically a fourth phase of the device placement process.

Once the disk space has been cleaned, the vertebral platforms of the adjacent vertebrae -1001-, -1002- are scraped (or stippled) (see FIG. 10). This can be done in various ways and with different tools. For example, as an alternative to the tool shown in FIG. 10, an osteotome may be used, for example the osteotome marketed under the name DFINE Midline®, or the like, to make multiple perforations in the platforms. Using this technique, new bone will grow from the platforms and will remain connected thereto.

Figure 11:
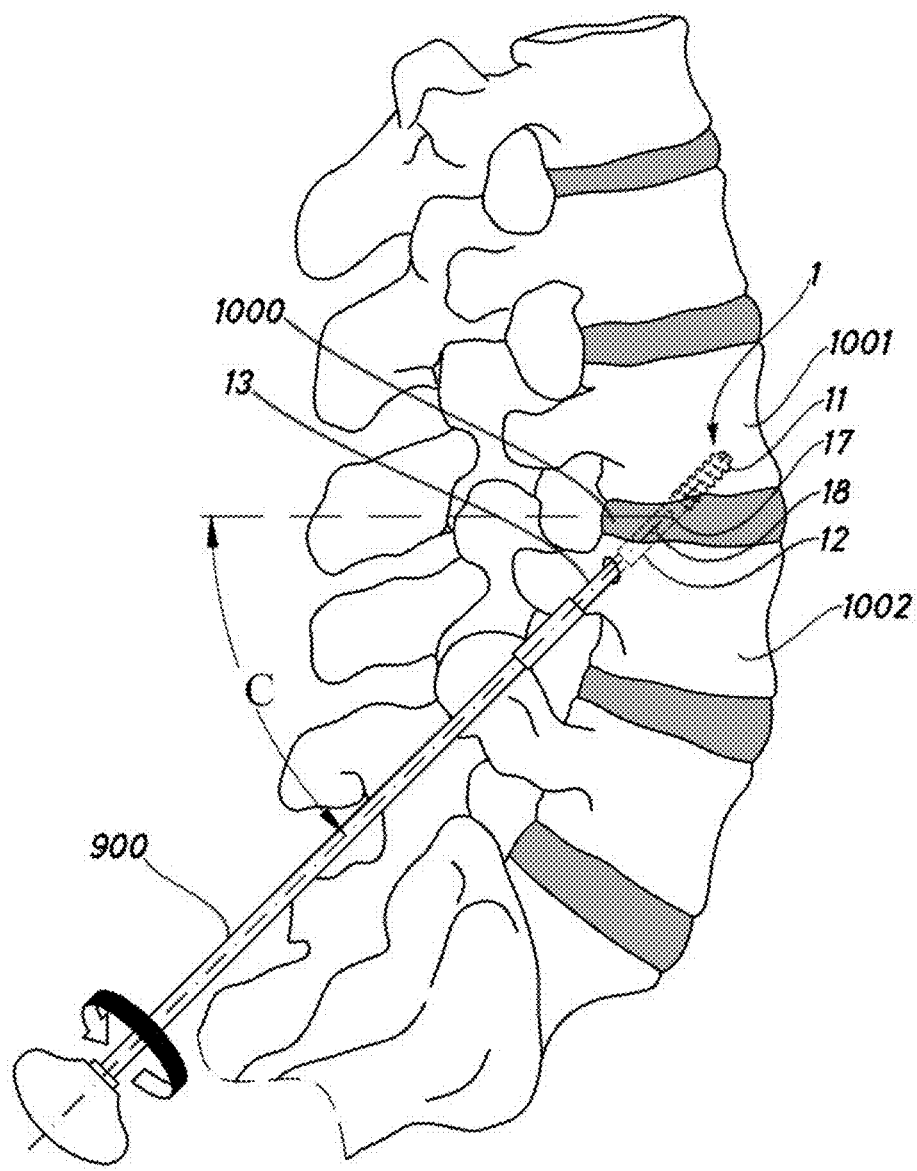
FIG. 11 shows diagrammatically a fifth phase of the device placement process.
Figure 12:
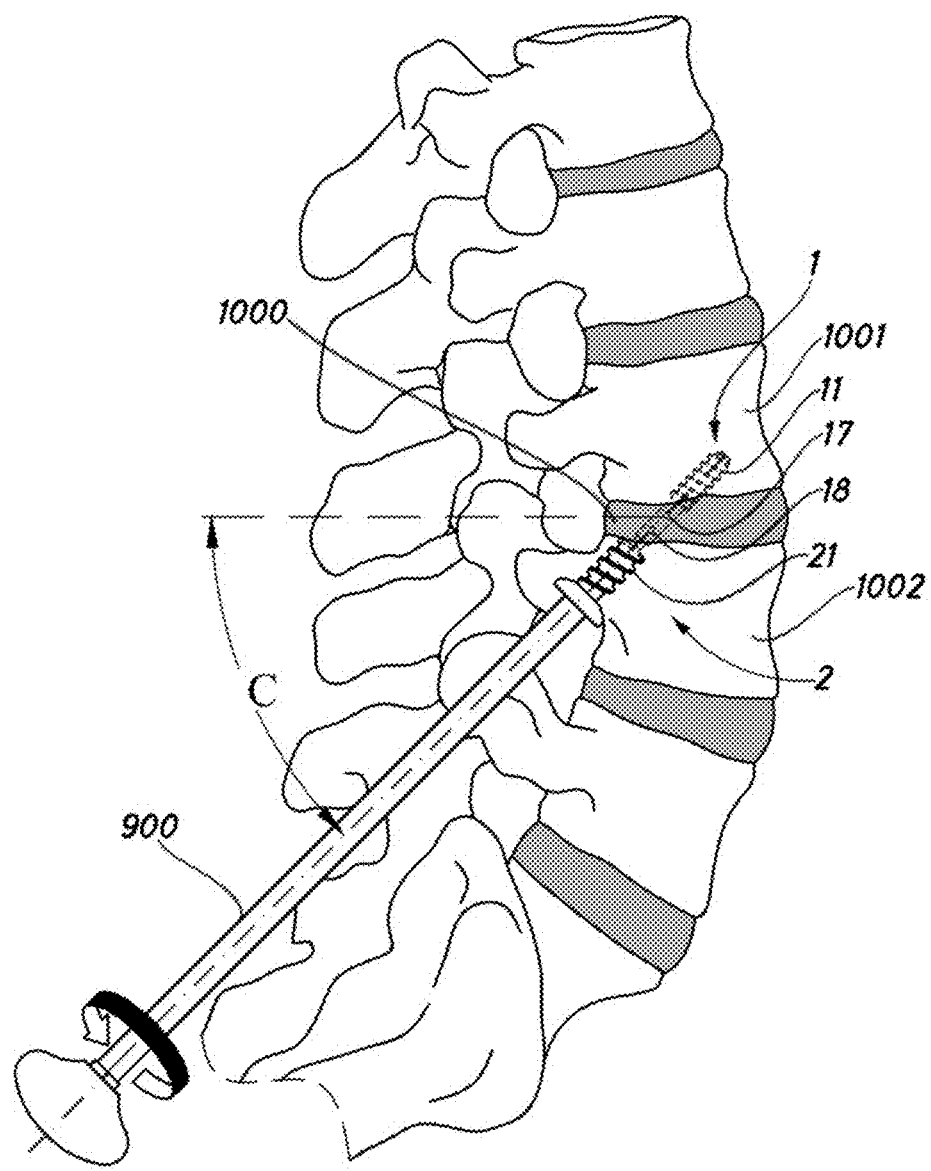
FIG. 12 shows diagrammatically a sixth phase of the device placement process.
Figure 13:
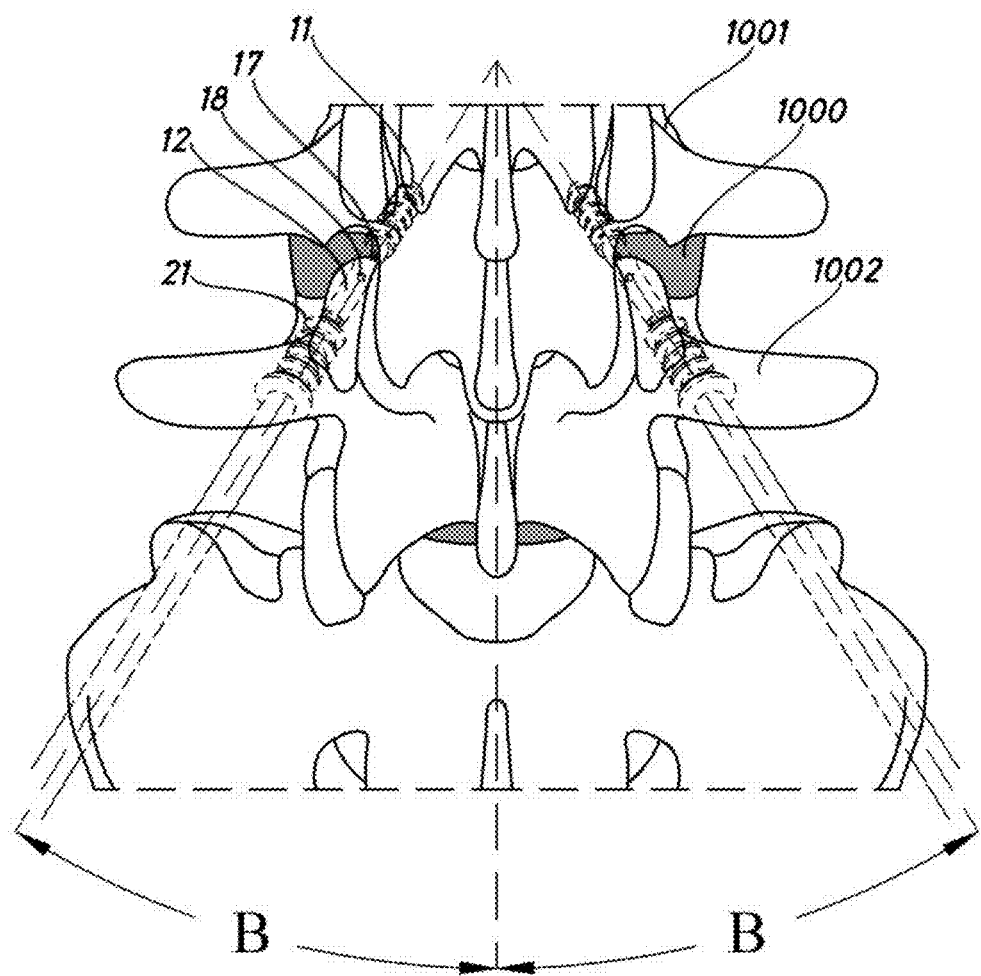
FIG. 13 shows diagrammatically a seventh phase of the device placement process.
Figure 14:
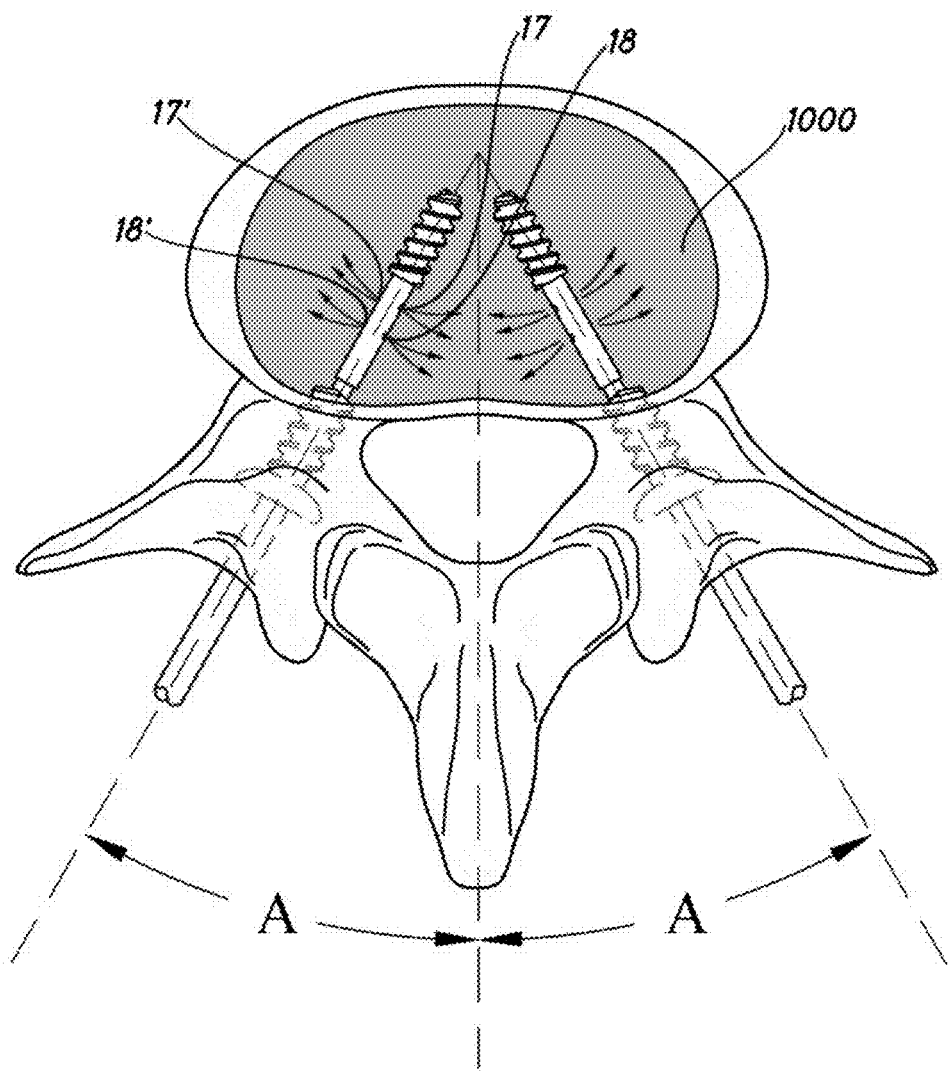
FIG. 14 shows diagrammatically an eighth phase of the device placement process.
Figure 15:
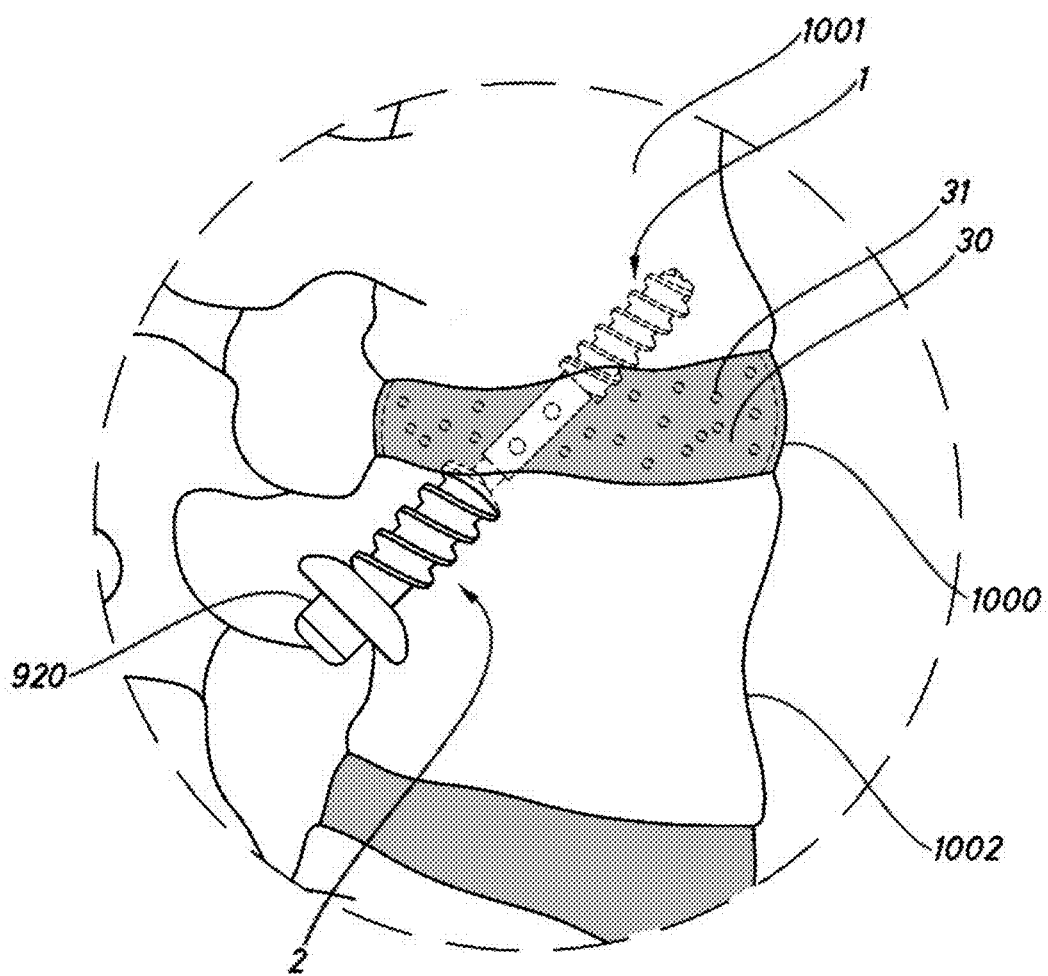
FIG. 15 shows from a lateral viewpoint a device according to the present invention already in place and prepared for the fusion of a vertebral level.
Figure 16:
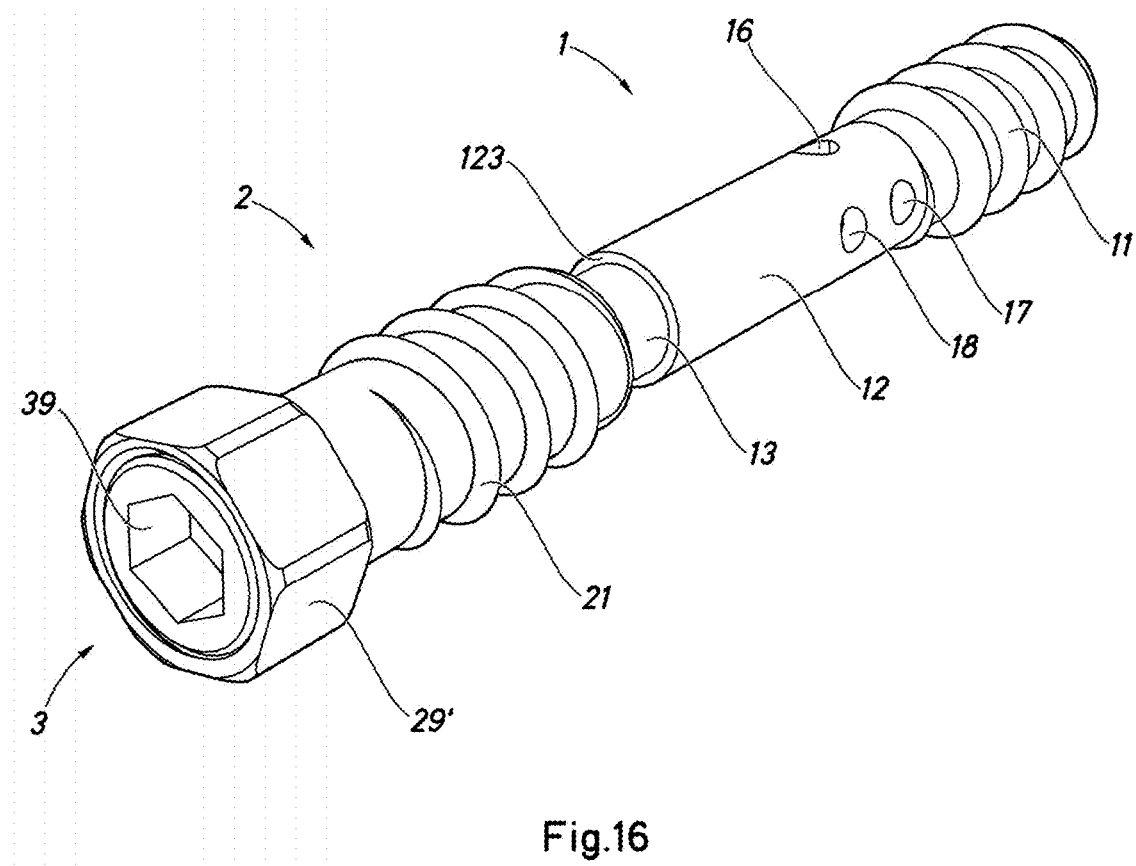
FIG. 16 is a perspective view of a second embodiment of a screw according to the present invention.
Figure 17:
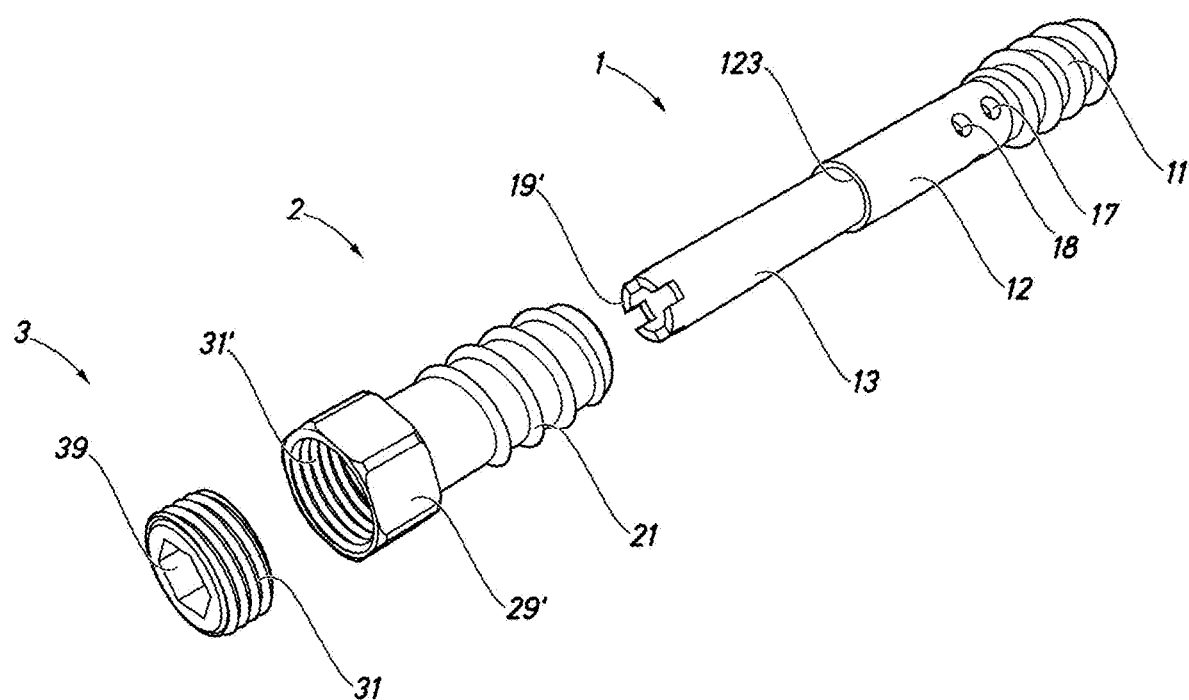
FIG. 17 is an exploded perspective view of the second embodiment.
Figure 18:
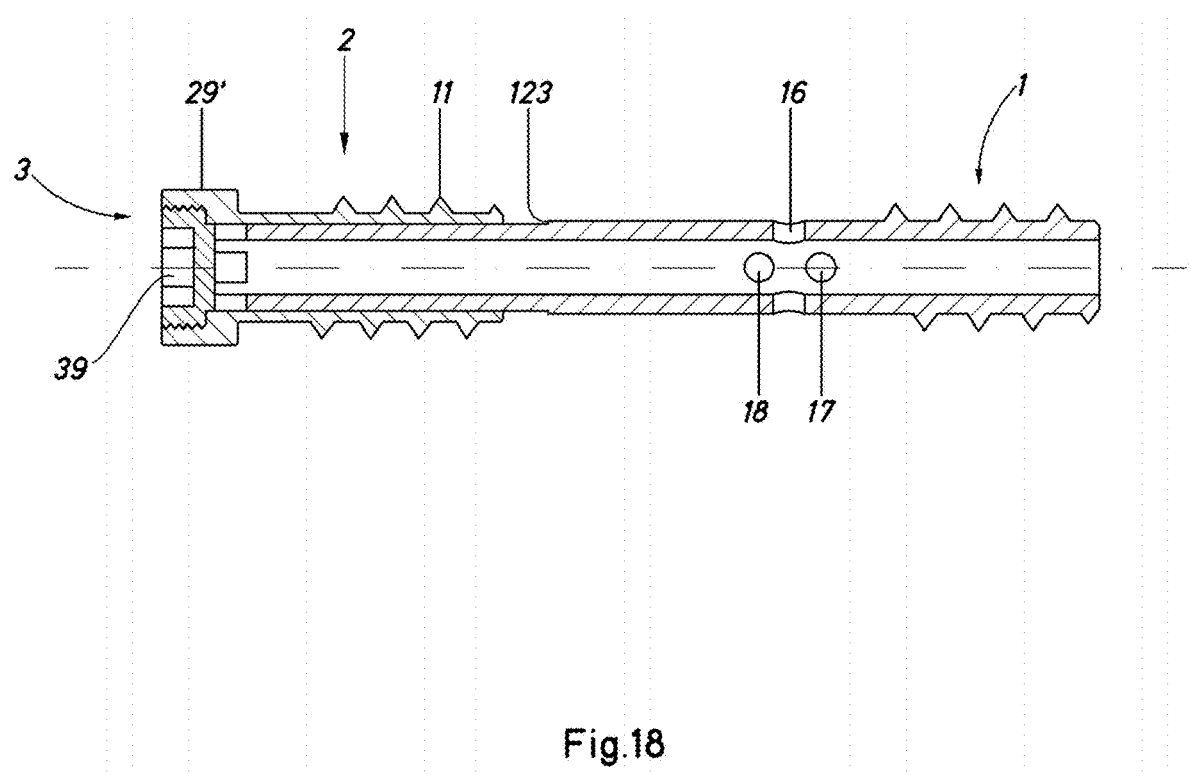
FIG. 18 is a view in cross section through the lateral mid-plane of the screw of the second embodiment.

Once the nucleus of the ring has been cleaned and the vertebral platforms have been scratched, the screw according to the present invention can be introduced up to the end of its travel (see FIG. 11 to 13).

Initially, the main body -1- enters until the distal thread -11- is threaded into the upper vertebra -1001- and the holes -17-, -18- are in the interior disk space -1000-. The bilateral placement process, with two screws, allows some correction of any vertebral deviations.

Next, the proximal body -2- is threaded inside the pedicle and the body of the lower vertebra -1002- until reaching the limit stop. Once the limit stop has been reached, it is possible to continue threading the proximal thread -21- against the limit stop. This creates a distraction which produces slight intervertebral lordosis. This effect is recommended, as most patients who require fusion have lost lordosis. The use of this over-threading also allows vertebral distractions to be corrected.

Once the screws have been put in place, the Kissner-type guide needle (not shown in the figures) can be removed and the void created in the disk space can be filled with a bone remodelling composition.

To produce the bone regeneration composition according to the present invention any type of polymerisable bone cement can be used. Polymerisation allows the cured bone cement to be introduced in a liquid or semi-liquid state with immediate hardening of the bone cement inside the intervertebral disk.

There are different grades of commercial polymers which are biocompatible and which, owing to the selection of components and/or additives, have polymerisation temperatures that are close to body temperature. Said polymers are generally commercialised in the form of a powder which must be mixed with a liquid polymerisation activator. Once the activator and powder have been mixed, with some commercial bone cements, the viscosity can be modified, for example by heating. An example of such a bone cement is that named StabiliT®, the main component of which is PMMA. The hardening time is under 30 minutes, which allows the relative position of the vertebrae to have consolidated by the end of the operation, which makes it possible to dispense with splints and exoskeletons during the bone formation period.

Control of viscosity may allow a bone-growth-promoting bed to be produced inside the disk which serves as a support including in cases where the ring is damaged. In particular, greater viscosity allows for controlled delivery and solidification before the composition leaves the disk space.

The process of producing the composition according to the present invention comprises the addition of a calcium phosphate provider, an oxygen provider and, optionally, an osteogenic factor and a contrast agent, more preferably, a non-ionic contrast agent.

For example, to produce a composition according to the present invention, StabiliT® bone cement (PMMA) is used, using a mixture of commercial activator with 5% by weight of oxygenated water as an activator, which is mixed with a mixture of StabiliT and hydroxyapatite powders at 20% by weight. It was observed that polymerisation was not stopped by the presence of oxygenated water. Once hardened, it was observed that greater porosity of the hardened bone cement was visible with the naked eye.

The same test was carried out by also adding blood-derived bone growth factors and a contrast agent (Lopamir or similar) to the activator liquid in quantities of less than 5%. Polymerisation was also successful.

Before the end of polymerisation the composition is introduced into the disk void that has been produced (see FIG. 4) while checking that said composition does not come out of the disk space limited and contained by the disk ring and waiting for a few minutes until polymerisation is complete. The composition comes out through the outlet fill holes -17-, -18-, -17'-, -18'-.

In addition, a cover -920- should be put in place which closes off access to the disk space by extraneous items.

Once hardened, the composition introduced inside the disk -1000- produces a bed -30- with numerous pores -31- in which bone will grow from the damaged areas of the platforms of the upper -1001- and lower -1002- vertebrae. Growth is maximised by the presence of oxygen and osteogenic growth factors inside the disk space and enhanced by the availability of calcium phosphate, preferably hydroxyapatite.

FIG. 16 to 23 show a second embodiment of the screw according to the present invention. Elements that are identical or similar and/or equivalent to those explained earlier have been identified with identical numerals and will not be explained in greater detail.

In the second embodiment, the proximal ends -19'-, -29'- of the main body -1- and of the proximal body respectively have been modified. In particular, the proximal end -19'- of the main body -1- does not project from/beyond the proximal body -2- and consists of an indented area. Furthermore, the proximal end -29'- of the proximal body -2- comprises a hexahedron-shaped outer portion for receiving an actuation tool and an inner thread -31'- for receiving, for example, a cover -3- (or other actuation tool).

The cover -3- has a thread -31- that fits with the inner thread -31'- of the proximal body and a hexahedral recess -39- for receiving an actuation tool.

Compared with the first embodiment shown in FIG. 1 to 15, an extra pair of holes -16- has been arranged positioned at 90° relative to the rest of the fill holes -17-, -18-.

Figure 19:
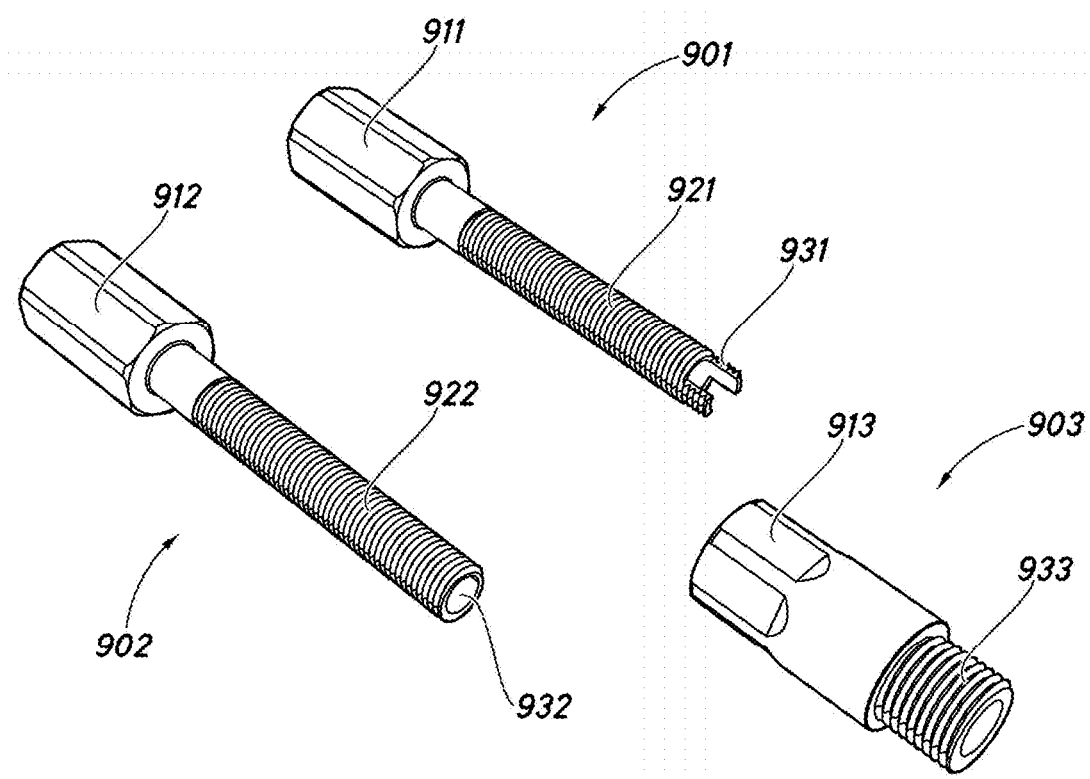
FIG. 19 is a perspective view of three auxiliary tools for actuating the screw of the second embodiment.

FIG. 19 shows three auxiliary tools, in particular, an adaptor head -903- and two actuation tools -901-, -902-, which can be used alternately. Either of the two actuation tools produces a relative movement between the main body -1- and the proximal body -2- of the screw, which also produces a relative rotation between the main body -11- and the proximal body -2- (using the auxiliary tool -901-) or not (using the auxiliary tool -902-).

More specifically, the adaptor head -903- comprises an outer surface which is adapted to a tool -913- (which has a hexagonal surface) and a thread -933- that fits with the inner thread -31- of the proximal end -29'- of the proximal body -2-. The body of the adaptor head is hollow, and has a through-hole with a section of internal thread (not visible in FIG. 19).

Both auxiliary tools -901-, -902- have tool adaptor heads -911-, -912- and threaded rods -921-, -922-, the thread of which fits with the thread of the through-hole of the adaptor head -903-. The distal ends -931-, -932- of both tools vary. In one case (-901-), the distal end -931- is indented and fits with the proximal end -19'- of the main body. In the other case (-902-), the distal end -932- is planar. As a result, both tools actuate the main body -1- differently.

Figure 20:
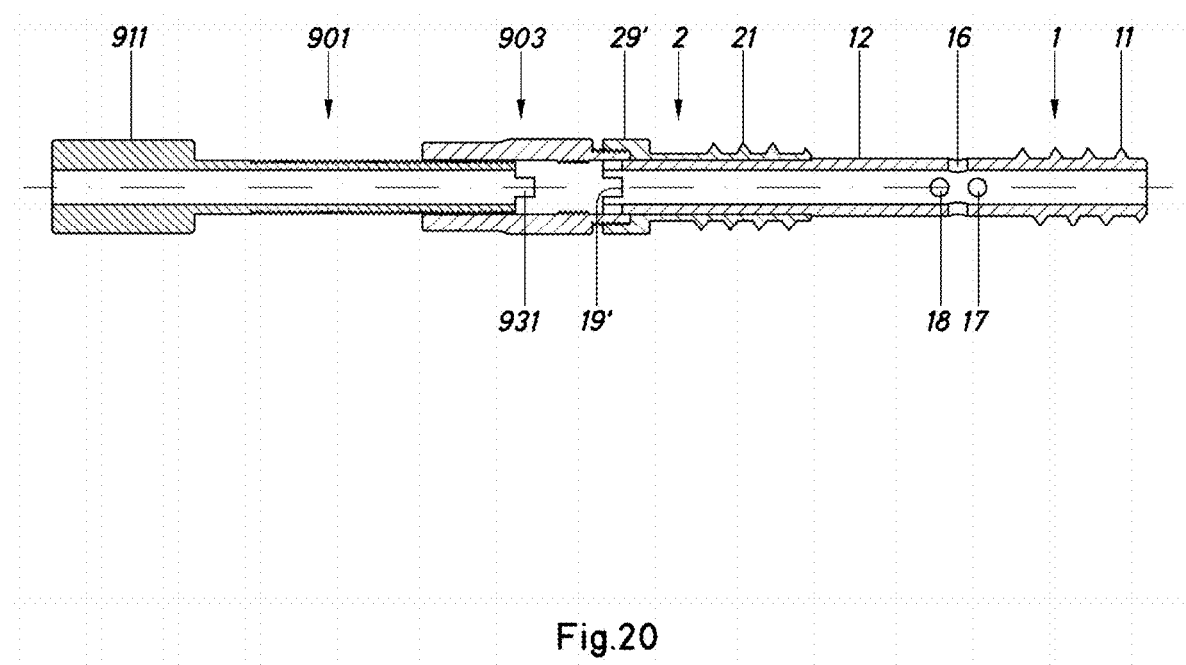
FIGS. 20 and 21 are diagrammatic views of a first method of actuating the screw of the second embodiment.
Figure 21:
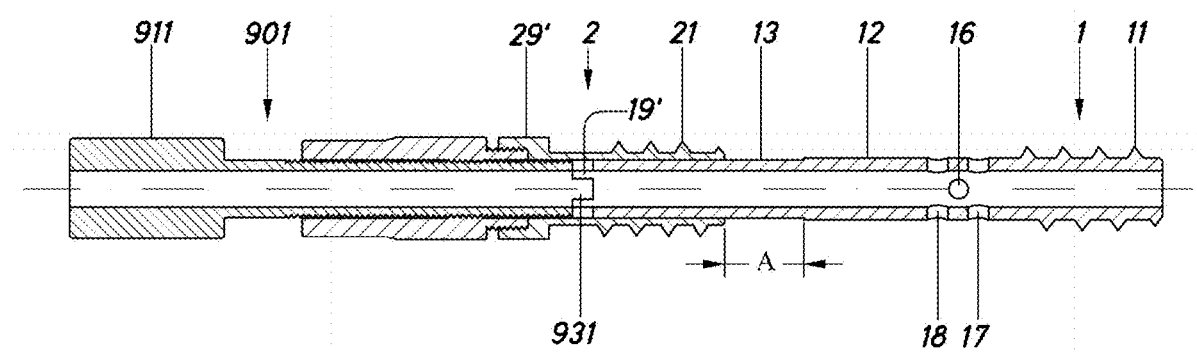

FIGS. 20 and 21 show the actuation produced by the first auxiliary tool -901-. The adaptor head -903- is threaded into the proximal head -29'- of the proximal body -2- and the threaded rod of the first auxiliary tool -901- is inserted in the through-hole of the adaptor head -903- until said rod reaches the internal threaded section, so that subsequent advances of the auxiliary tool -901- must be made by rotation. When the distal end -931- of the first auxiliary tool -901- touches the proximal end -19- of the main body, the indented elements fit together, which means that the main body -1- as well as moving relative to the proximal body -2- (increasing the distance -A-) rotates drawn by the first auxiliary tool -901-, as can be seen by comparing FIGS. 20 and 21, in which the angular position of the fill holes -16-, -17-, -18, changes.

Figure 22:
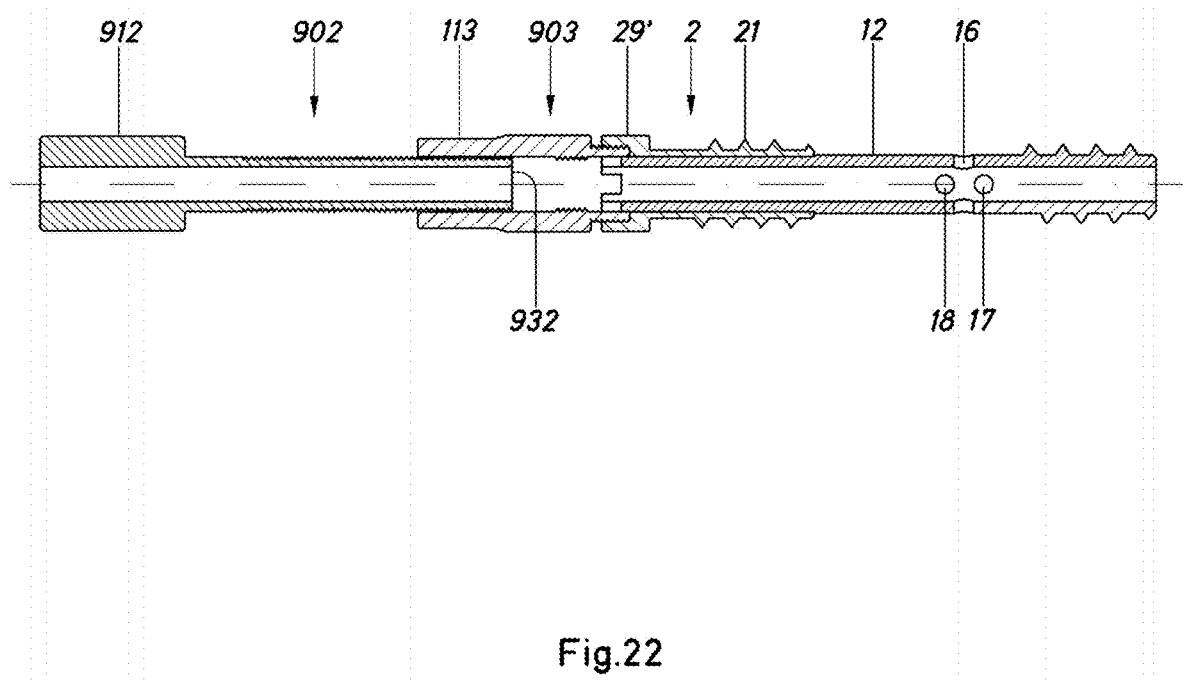
FIGS. 22 and 23 are diagrammatic views of a second method of actuating the screw of the second embodiment.
Figure 23:
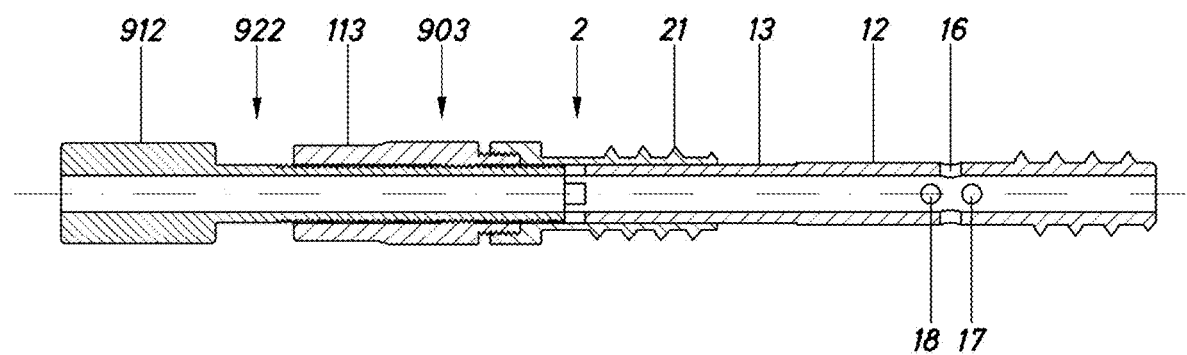

FIGS. 22 and 23 show the equivalent process with the second auxiliary tool -902-, the distal end -932- of which is planar and not hollowed out. In this case, the second auxiliary tool pushes the main body -9-, but without transmitting any rotation thereto. Using the first auxiliary tool -901- it is possible to go deeper into the thread of the main body into the corresponding vertebra, whereas with the second auxiliary tool -902- the distance between vertebrae can be increased.

Figure 24:
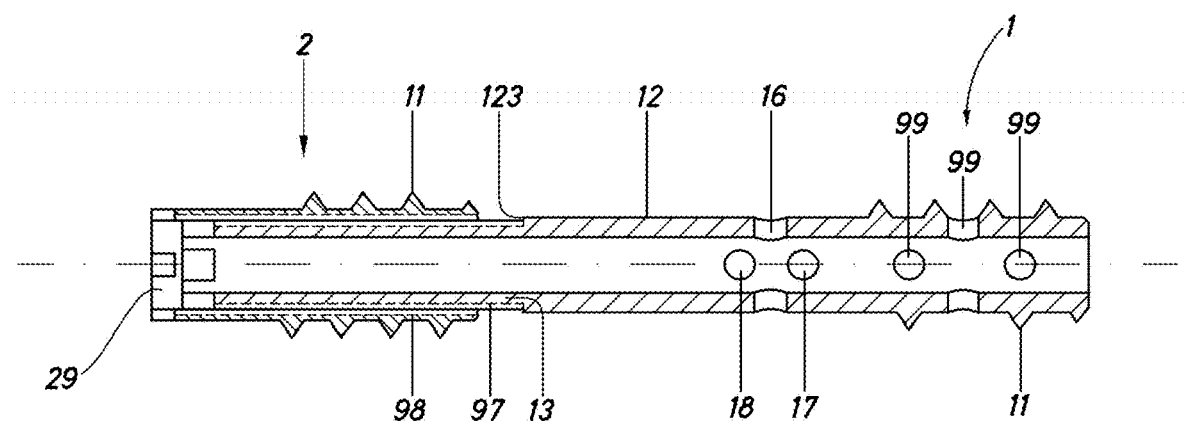
FIG. 24 shows a third embodiment of a screw according to the present invention.

FIG. 24 shows a third embodiment of a screw according to the present invention. Elements that are the same or equivalent to those shown in previous figures will be identified with identical numerals and will therefore not be described in detail.

In this embodiment auxiliary fill holes -99- have been arranged in the thread area -11- of the main body -1-. Said holes are useful in cases of osteoporosis which require distal cementing of the vertebral body. Said holes -19- may, of course, be implemented in other embodiments, for example, in those shown above.

Another modification compared with the previous embodiments is to add various threads -98-, -97- that fit together between the proximal body -2- and the main body -1-. This causes movement between both bodies to also be associated with a rotation between both portions. In addition, the proximal end -29- of the main body has an internal surface for receiving an actuation tool, for example a standard tool.

The use of two concentric external sleeves -1001-, -1002-, one inside the other (not shown in the figure) is therefore possible in order to advance both portions of the screw simultaneously while, nevertheless, being able to screw the main body -1-, the proximal body -2- independently to the bone, or both bodies at the same time.

Figure 25:
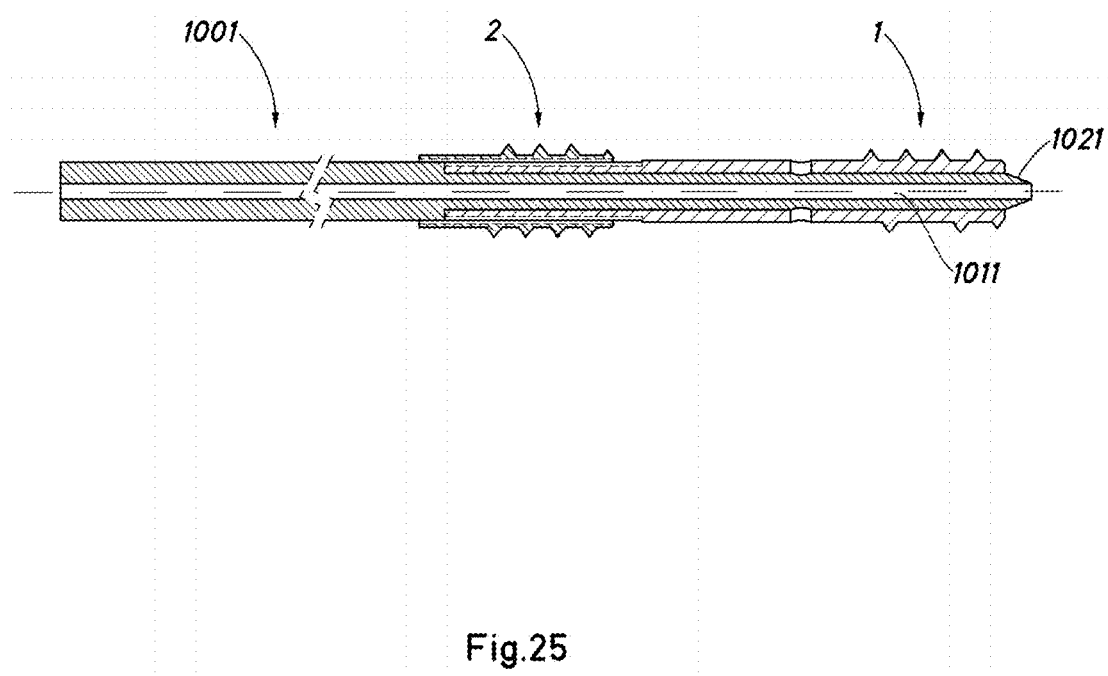
FIG. 25 to 27 show diagrammatically a process of putting in place the third embodiment, using two concentric sleeves.
Figure 26:
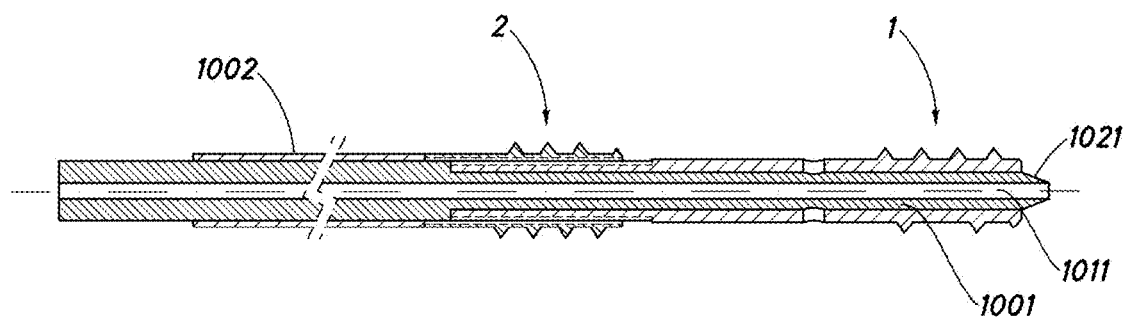
Figure 27:
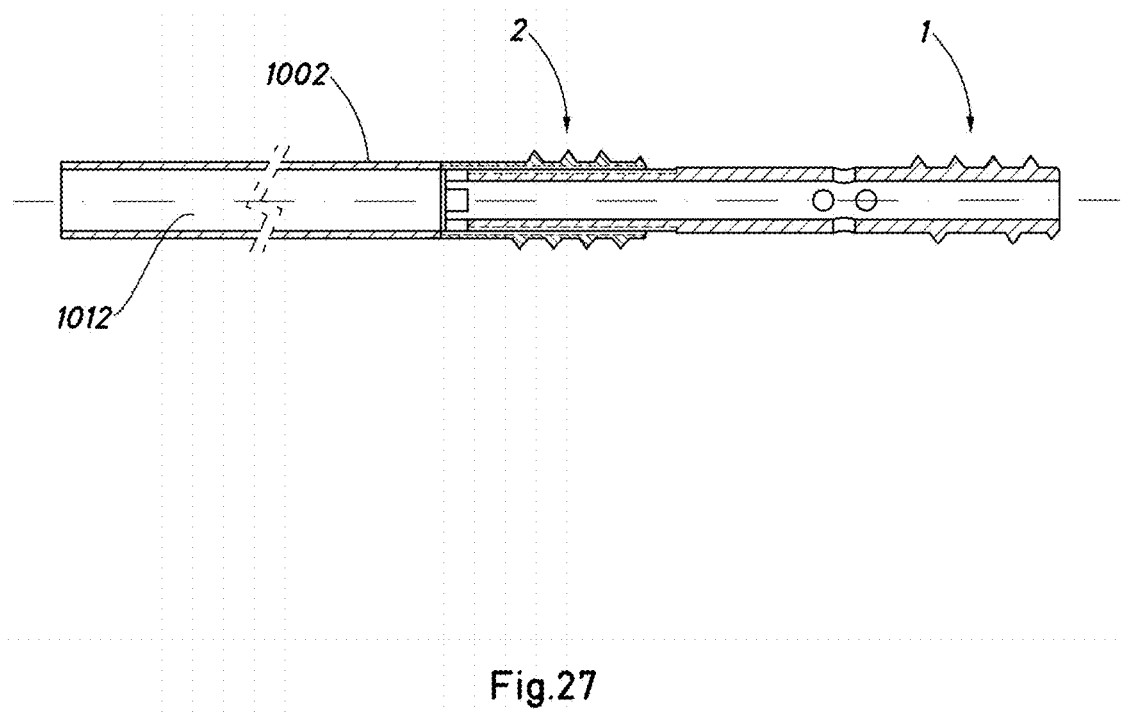

FIG. 25 to 27 show diagrammatically a process for the placement of a screw according to the present invention using two concentric sleeves -1001-, -1002-. The sleeves have been shown diagrammatically and without detail. It will be understood that the distal ends thereof are of a suitable shape to actuate the different bodies of the screw -1-, -2-.

With reference to FIG. 25, the screw is put in place with the aid of the internal sleeve -1001- (or alternatively the screw is put in place by other means after the internal sleeve -1001- has been put in place). The internal sleeve has a central through-hole -1011- in which the bolt that was inserted initially is housed and is used for testing the screw and internal sleeve -1001-. The internal sleeve -1001- has a pointed or conical distal end -1021- to prevent the through-hole of the screw from being blocked by unwanted particles from the patient's body. The screw may also have a conical distal point. Next (see FIG. 26), the outer sleeve -1002-, which has a through-hole -1012- in which the inner sleeve -1001- is housed, is put in place.

With the two sleeves in position, the main body of the screw can be threaded and/or moved forward (by means of the inner sleeve) or the proximal body (by means of the outer sleeve) or both at the same time (with both sleeves being actuated simultaneously). This can be achieved using tools at the proximal end that are known in the field of non-invasive surgery.

Once the screw is in place, the inner sleeve -1001- and the bolt (not shown in FIG. 25 to 27) are withdrawn, leaving the outer sleeve -1002- in place, and the through-hole thereof -1012- is used as a guide for the bone filler or tool for injecting the bone cement or substance for treating the interdiskal space and/or vertebra. Next, the outer sleeve is withdrawn.

The divergent characteristics of the embodiments shown are applicable to other embodiments shown, either grouped together or individually.

The installation process may be different from that shown, and different percutaneous techniques or even non-percutaneous techniques may also be used. The order of the operations is also subject to change.

Although the invention has been described with respect to preferred embodiments, said embodiments should not be considered as limiting the invention, which will be defined by the widest interpretation of the following claims.

What is claimed is:

1. A process of bone creation between adjacent vertebrae using an intervertebral stabilizing screw which comprises:
    a main body with an axial through hole and a distal thread located at a distal end of the main body,
    a hollow proximal secondary body that can slide along the length of the main body, and
    a travel stop for the proximal secondary body, located on an outer surface of the main body,
        wherein the proximal secondary body further comprises an external thread, and said main body comprises at least one fill hole, located between the distal thread and said stop,
    the process comprising:
    installing a guide passing through inside of a disk located between the adjacent vertebrae,
    ablating material inside of the disk,
    cleaning inside of the disk,
    scraping vertebral platforms of the adjacent vertebrae,
    inserting the main body until the distal thread is secured to an upper vertebrae of the adjacent vertebrae such that the at least one fill hole is in inside of the disk,
    inserting the proximal body until reaching to the limit stop such that the proximal body is threaded inside of a pedicle and secured to a lower vertebrae of the adjacent vertebrae,
    removing the guide, and
    injecting a bone remodeling composition into inside of the disk through the axial hole and the at least one fill hole.

2. The process according to claim 1, wherein the ablation of the material inside of disk is carried out by applying radiofrequency or inserting, a cannula into inside of the disk.

3. The process according to claim 1, wherein the ablation of the material inside of disk is carried out by inserting two cannulas into inside of the disk.

4. The process according to claim 3, wherein the cleaning inside of the disk comprises:
    injecting a cleaning fluid into one of the two cannulas, and
    removing the cleaning fluid from the other one of the two cannulas.

5. The process according to claim 1, further comprising putting a cover at proximal end of the main body to closes off access to inside of the disk by extraneous items.

6. The process according to claim 1, further comprising continuously inserting the proximal body against the limit stop alter reaching to the limit stop whereby a distraction which produces slight intervertebral lordosis is created.

* * * * *